(12) United States Patent
Skinner et al.

(10) Patent No.: US 7,938,175 B2
(45) Date of Patent: May 10, 2011

(54) DRILLING, PERFORATING AND FORMATION ANALYSIS

(75) Inventors: Neal G. Skinner, Lewisville, TX (US); Harry D. Smith, Jr., Montgomery, TX (US); Christopher M. Jones, Missouri City, TX (US); Daniel D. Gleitman, Houston, TX (US); Michael T Pelletier, Houston, TX (US)

(73) Assignee: Halliburton Energy Services Inc., Duncan, OK (US)

( * ) Notice: Subject to any disclaimer, the term of this patent is extended or adjusted under 35 U.S.C. 154(b) by 188 days.

(21) Appl. No.: 12/359,968

(22) Filed: Jan. 26, 2009

(65) Prior Publication Data

US 2009/0133871 A1   May 28, 2009

Related U.S. Application Data

(63) Continuation of application No. 10/987,923, filed on Nov. 12, 2004, now Pat. No. 7,490,664.

(51) Int. Cl.
*E21B 36/00* (2006.01)
*E21B 47/00* (2006.01)

(52) U.S. Cl. .......... 166/57; 166/250.16; 175/12; 175/50

(58) Field of Classification Search ............... 166/253.1, 166/250.16, 298, 55, 55.1, 57; 175/12, 15, 175/20, 17, 50, 58
See application file for complete search history.

(56) References Cited

U.S. PATENT DOCUMENTS

| | | | |
|---|---|---|---|
| 3,461,964 A | 8/1969 | Venghiattis |
| 3,493,060 A | 2/1970 | Van Dyk |
| 3,693,718 A | 9/1972 | Stout |
| 3,871,485 A | 3/1975 | Keenan, Jr. |
| 3,882,945 A | 5/1975 | Keenan, Jr. |
| 3,960,448 A | 6/1976 | Schmidt et al. |
| 3,977,478 A | 8/1976 | Shuck |
| 3,992,095 A | 11/1976 | Jacoby et al. |
| 3,998,281 A | 12/1976 | Salisbury et al. |
| 4,026,356 A | 5/1977 | Shuck |
| 4,061,190 A | 12/1977 | Bloomfield |

(Continued)

FOREIGN PATENT DOCUMENTS

EP   0 950 170 B1   9/2002

(Continued)

OTHER PUBLICATIONS

Brian C. Gahan, et al., "Laser Drilling: Determination of Energy Required to Remove Rock," SPE 71466, Society of Petroleum Engineers, copyright 2001, pp. 1-11.

(Continued)

*Primary Examiner* — Daniel P Stephenson
(74) *Attorney, Agent, or Firm* — John W. Wustenberg; Fish & Richardson P.C.

(57) ABSTRACT

A system and method of drilling and/or perforating uses a laser beam to remove material, such as to perforate the casing, cement and formation or drill a well bore. The system and method can further or alternately encompass material analysis that can be performed without removing the material from the well bore. The analysis can be performed apart from or in connection with drilling operations and/or perforating the casing, cement and formation. The analysis can be used in a feed back loop to adjust material removal, adjust material analysis, determine the location of future material removal, and for other uses.

27 Claims, 11 Drawing Sheets

U.S. PATENT DOCUMENTS

| | | | |
|---|---|---|---|
| 4,066,138 A | 1/1978 | Salisbury et al. | |
| 4,090,572 A * | 5/1978 | Welch | 175/16 |
| 4,113,036 A | 9/1978 | Stout | |
| 4,189,705 A | 2/1980 | Pitts, Jr. | |
| 4,199,034 A | 4/1980 | Salisbury et al. | |
| 4,227,582 A | 10/1980 | Price | |
| 4,228,856 A | 10/1980 | Reale | |
| 4,266,609 A | 5/1981 | Rom et al. | |
| 4,282,940 A | 8/1981 | Salisbury et al. | |
| 4,370,886 A | 2/1983 | Smith, Jr. et al. | |
| 4,375,164 A | 3/1983 | Dodge et al. | |
| 4,860,654 A | 8/1989 | Chawla et al. | |
| 4,860,655 A | 8/1989 | Chawla | |
| 5,049,738 A | 9/1991 | Gergely et al. | |
| 5,084,617 A | 1/1992 | Gergely | |
| 5,107,936 A | 4/1992 | Foppe | |
| 5,163,321 A | 11/1992 | Perales | |
| 5,172,112 A | 12/1992 | Jennings | |
| 5,396,805 A | 3/1995 | Surjaatmadja | |
| 5,413,045 A | 5/1995 | Miszewski | |
| 5,479,860 A | 1/1996 | Ellis | |
| 5,561,516 A | 10/1996 | Noble et al. | |
| 5,757,484 A | 5/1998 | Miles et al. | |
| 5,847,825 A | 12/1998 | Alexander | |
| 5,862,273 A | 1/1999 | Pelletier | |
| 5,929,986 A | 7/1999 | Slater et al. | |
| 5,986,756 A | 11/1999 | Slater et al. | |
| 6,038,363 A | 3/2000 | Slater et al. | |
| 6,147,754 A | 11/2000 | Theriault et al. | |
| 6,166,546 A | 12/2000 | Scheihing et al. | |
| 6,250,391 B1 | 6/2001 | Proudfoot | |
| 6,321,839 B1 | 11/2001 | Vereecken et al. | |
| 6,355,928 B1 | 3/2002 | Skinner et al. | |
| 6,384,738 B1 | 5/2002 | Carstensen et al. | |
| 6,437,326 B1 | 8/2002 | Yamate et al. | |
| 6,450,257 B1 | 9/2002 | Douglas | |
| 6,644,848 B1 | 11/2003 | Clayton et al. | |
| 6,710,720 B2 | 3/2004 | Carstensen et al. | |
| 6,729,400 B2 * | 5/2004 | Mullins et al. | 166/264 |
| 6,747,743 B2 | 6/2004 | Skinner et al. | |
| 6,755,262 B2 | 6/2004 | Parker | |
| 6,847,034 B2 | 1/2005 | Shah et al. | |
| 6,851,488 B2 | 2/2005 | Batarseh | |
| 6,867,858 B2 | 3/2005 | Owen et al. | |
| 6,874,361 B1 | 4/2005 | Meltz et al. | |
| 6,880,646 B2 | 4/2005 | Batarseh | |
| 6,888,097 B2 | 5/2005 | Batarseh | |
| 6,888,127 B2 | 5/2005 | Jones et al. | |
| 6,912,898 B2 | 7/2005 | Jones et al. | |
| 6,913,079 B2 | 7/2005 | Tubel | |
| 6,957,576 B2 | 10/2005 | Skinner et al. | |
| 6,967,322 B2 | 11/2005 | Jones et al. | |
| 6,978,832 B2 | 12/2005 | Gardner et al. | |
| 6,994,162 B2 | 2/2006 | Robison | |
| 7,147,064 B2 | 12/2006 | Batarseh et al. | |
| 7,210,343 B2 | 5/2007 | Shammai et | |
| 2002/0039465 A1 | 4/2002 | Skinner | |
| 2002/0189806 A1 | 12/2002 | Davidson et al. | |
| 2003/0000741 A1 | 1/2003 | Rosa | |
| 2003/0094281 A1 | 5/2003 | Tubel | |
| 2003/0132029 A1 | 7/2003 | Parker | |
| 2004/0006429 A1 | 1/2004 | Brown | |
| 2004/0016295 A1 | 1/2004 | Skinner et al. | |
| 2004/0020643 A1 | 2/2004 | Thomeer et al. | |
| 2004/0033017 A1 | 2/2004 | Kringlebotn et al. | |
| 2004/0093950 A1 | 5/2004 | Bohnert | |
| 2004/0119471 A1 | 6/2004 | Blanz et al. | |
| 2004/0129418 A1 | 7/2004 | Jee et al. | |
| 2004/0195003 A1 * | 10/2004 | Batarseh | 175/16 |
| 2004/0206505 A1 | 10/2004 | Batarseh | |
| 2004/0207731 A1 | 10/2004 | Bearman et al. | |
| 2004/0211894 A1 | 10/2004 | Hother et al. | |
| 2004/0218176 A1 | 11/2004 | Shammai et al. | |
| 2004/0244970 A1 | 12/2004 | Smith, Jr. | |
| 2004/0252748 A1 | 12/2004 | Gleitman | |
| 2004/0256103 A1 | 12/2004 | Batarseh | |
| 2005/0012244 A1 | 1/2005 | Jones | |
| 2005/0094129 A1 | 5/2005 | MacDougall | |
| 2005/0099618 A1 | 5/2005 | DiFoggio et al. | |
| 2005/0230107 A1 | 10/2005 | McDaniel et al. | |
| 2005/0252286 A1 | 11/2005 | Ibrahim et al. | |
| 2005/0268704 A1 | 12/2005 | Bissonnette et al. | |
| 2005/0269132 A1 | 12/2005 | Batarseh et al. | |
| 2005/0272512 A1 | 12/2005 | Bissonnette et al. | |
| 2005/0272513 A1 | 12/2005 | Bissonnette et al. | |
| 2005/0272514 A1 | 12/2005 | Bissonnette et al. | |
| 2005/0282645 A1 | 12/2005 | Bissonnette et al. | |
| 2006/0038997 A1 | 2/2006 | Julian et al. | |
| 2006/0231257 A1 | 10/2006 | Reed et al. | |
| 2006/0237233 A1 | 10/2006 | Reed et al. | |
| 2010/0193186 A1 * | 8/2010 | Smith | 166/254.2 |

FOREIGN PATENT DOCUMENTS

| | | |
|---|---|---|
| JP | 09072738 A | 3/1997 |
| WO | WO 97/49893 | 12/1997 |
| WO | WO 98/50673 | 11/1998 |
| WO | WO 02/057805 | 7/2002 |
| WO | WO 2004/009958 A1 | 1/2004 |
| WO | WO 2006/008155 A1 | 1/2006 |
| WO | WO 2006/054079 A1 | 5/2006 |

OTHER PUBLICATIONS

Ramona M. Graves, et al., "Temperatures Induced by High Power Lasers: Effects on Reservoir Rock Strength and Mechanical Properties," SPE/ISRM 78154, Society of Petroleum Engineers, copyright 2002, pp. 1-7.

Industry Consortium Forum, Improving Oil and Gas Well Perforations with High-Energy Lasers, Gas Technology Institute, May 14, 2002, 5 pages.

Brian C. Gahan, "Laser Drilling: Understanding Laser/Rock Interaction Fundamentals," Gas TIPS, Spring 2002, pp. 4-8.

Fiber Optic Sensors: An Introduction for Engineers and Scientists, Wiley Series in Pure and Applied Optics, Copyright 1991 by John Wiley & Sons, Inc., 11 pages.

Z. Xu, et al., "Specific Energy for Laser Removal of Rocks," 20th International Congress on Applications of Lasers and Electro-Optics, Jacksonville, Florida, Oct. 15-18, 2001, 8 pages.

B.C. Gahan, et al., "Laser Drilling: Drilling with the Power of Light Phase 1: Topical Report," DOE Cooperative Agreement No. DE-FC-26-00NT40917, Sep. 2001, 150 pages.

Halliburton, LaserStrat™ Service, Oct. 16, 2003, 3 pages.

Halliburton, LaserStrat™ Service, "Chemical Fingerprinting and Chemostratigraphic Correlation of Formations,", Oct. 16, 2003, 4 pages.

John Dakin and Brian Culshaw, "Optical Fiber Sensors Volume Four Applications, Analysis, and Future Trends," Sections 7.2-7.1.1.2; copyright 1997, 8 pages.

Search Report Under Section 17(5) for application No. GB0523070.1 mailed Jan. 23, 2006, 4 pages.

Website: http://www.ipgphotonics.com/products_telecom_modules_lasers.htm, "Lasers", copyrighted by IPG Potonics Corporation, printed on Jan. 30, 2009, 1 page.

Website: http://www.ipgphotonics.com/products_telecom_rack_lasers.htm, "Rack Mounted Lasers", copyrighted by IPG Photonics Corporation, printed on Jan. 30, 2009, 1 page.

Website: http://www.ipgphotonics.com/products_telecom_raman_RLT_M_Series_Raman_Laser_Mo.htm, "RLT-M Series 0.5W to 10W Raman Fiber Laser Modules", copyrighted by IPG Photonics Corporation, printed on Jan. 30, 2009, 1 page.

Website: http://www.ipgphotonics.com/products_telecom_raman_RLT_R_Series_Raman_Laser_Ra.htm. "RLT-M Series Raman Laser Rack Mount", copyrighted by IPG Photonics Corporation, printed on Jan. 30, 2009, 1 page.

Website: http://www.ipgphotonics.com/prod_tel_raman_rlm_series.htm, "RLM Series 1 to 10 Watts Single and Dual Wavelength Raman Fiber Laser", copyrighted by IPG Photonics Corporation, printed on Jan. 30, 2009, 2 pages.

Website: http://www.ipgphotonics.com/products_1micron_lasers_pulsed.htm, "1 Micron Lasers CW", copyrighted by IPG Photonics Corporation, printed on Jan. 30, 2009, 1 page.

Website: http://www.ipgphotonics.com/products_1micron_lasers_cw.htm, "1 Micron Lasers CW", copyrighted by IPG Photonics Corporation, printed on Jan. 30, 2009, 1 page.
Website: http://www.ipgphotonics.com/products_1micron_lasers_single.htm, "YLR LP-SF Series: 1 to 150W Single Frequency Linearly Polarized Ytterbium Fiber Laser", copyrighted by IPG Photonics Corporation, printed on Jan. 30, 2009, 1 page.
Website: http://www.ipgphotonics.com/products_15micron_lasers_cw.htm, "1.5 Microns Lasers CW", copyrighted by IPG Photonics Corporation, printed on Jan. 30, 2009, 1 page.
Website: http://www.ipgphotonics.com/products_15micron_lasers_pulsed.htm, "ELP Series: 0.1-0.5 mJ Pulsed Erbium Fiber Laser", copyrighted by IPG Photonics Corporation, printed on Jan. 30, 2009, 2 pages.
Website: http://www.ipgphotonics.com/products_15micron_lasers_single.htm, "ELR SF Series: 1-100 Watt Single Frequency Erbium Fiber Laser", copyrighted by IPG Photonics Corporation, printed on Jan. 30, 2009, 2 pages.
Website: http://www.ipgphotonics.com/products_15micron_lasers_tunable.htm, "ELT Series: 100 mW to 25 W C+L Band Tunable Erbium Fiber Lasers", copyrighted by IPG Photonics Corporation, printed on Jan. 30, 2009, 2 pages.
Website: http://www.ipgphotonics.com/products_2micron_laser_cw.htm, "2 Microns Lasers CW", copyrighted by IPG Photonics Corporation, printed on Jan. 30, 2009, 1 page.
Website: http://www.ipgphotonics.com/products_2micron_laser_tunable.htm, "TLT Series: 0.1-20W Tunable Thulium Fiber Lasers", copyrighted by IPG Photonics Corporation, printed on Jan. 30, 2009, 1 page.
Website: http://www.ipgphotonics.com/products_ipld_9_series.htm, "IPLD-9 Series: 9W High Power Multimode Laser Diodes", copyrighted by IPG Photonics Corporation, printed on Jan. 30, 2009, 2 pages.
Website: http://www.ipgphotonics.com/products_09micron_ipld_20_series.htm, "IPLD-20 Series: 20W High Power Multimode Laser Diodes", copyrighted by IPG Photonics Corporation, printed on Jan. 30, 2009, 2 pages.
Website: http://www.ipgphotonics.com/09_micron_direct_diode.htm, "Direct diode fiber delivered at 980 nanometers", copyrighted by IPG Photonics Corporation, printed on Jan. 30, 2009, 1 page.
Website: http://www.ipgphotonics.com/apps_mat_diode_dir_series.htm, "DLR Series: 5W to 10kW Direct Diode Fiber Pigtailed Laser Systems", copyrighted by IPG Photonics Corporation, printed on Jan. 30, 2009, 1 page.
Website: http://www.ipgphotonics.com/apps_mat_lab_cutting.htm, "Laser Cutting with Ytterbium Lasers", copyrighted by IPG Photonics Corporation, printed on Jan. 30, 2009, 2 pages.
Website: http://www.ipgphotonics.com/apps_mat_lab_drilling.htm, "Laser Drilling with Ytterbium Lasers", copyrighted by IPG Photonics Corporation, printed on Jan. 30, 2009, 2 pages.
Abbreviated Examination Report under Section 18(3) for GB0523071.1, Nov. 3, 2009, 1 page.

* cited by examiner

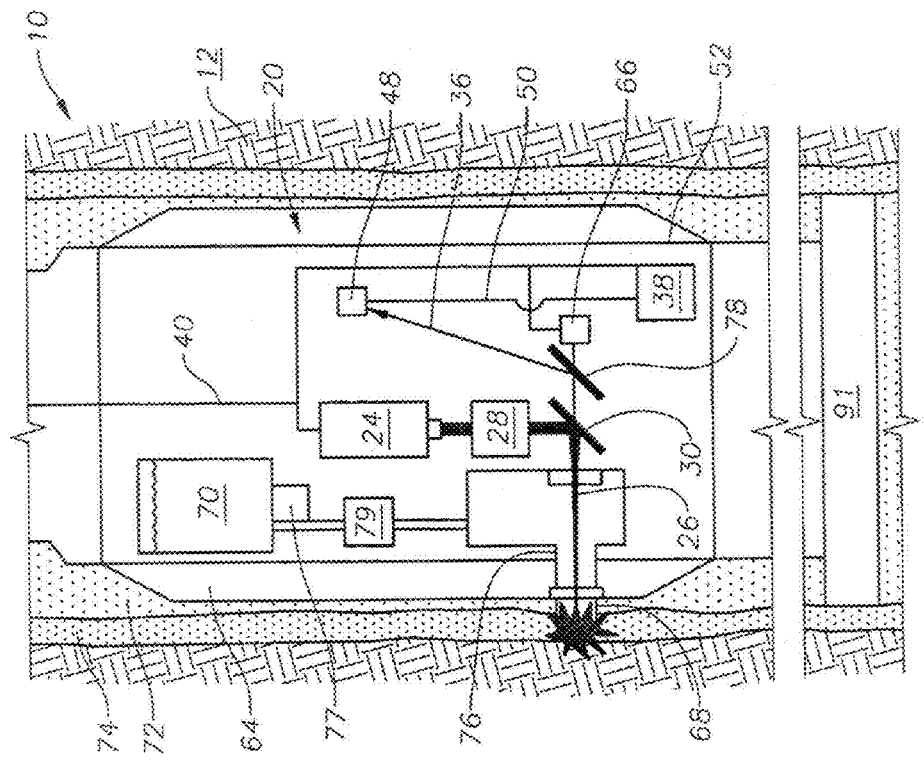
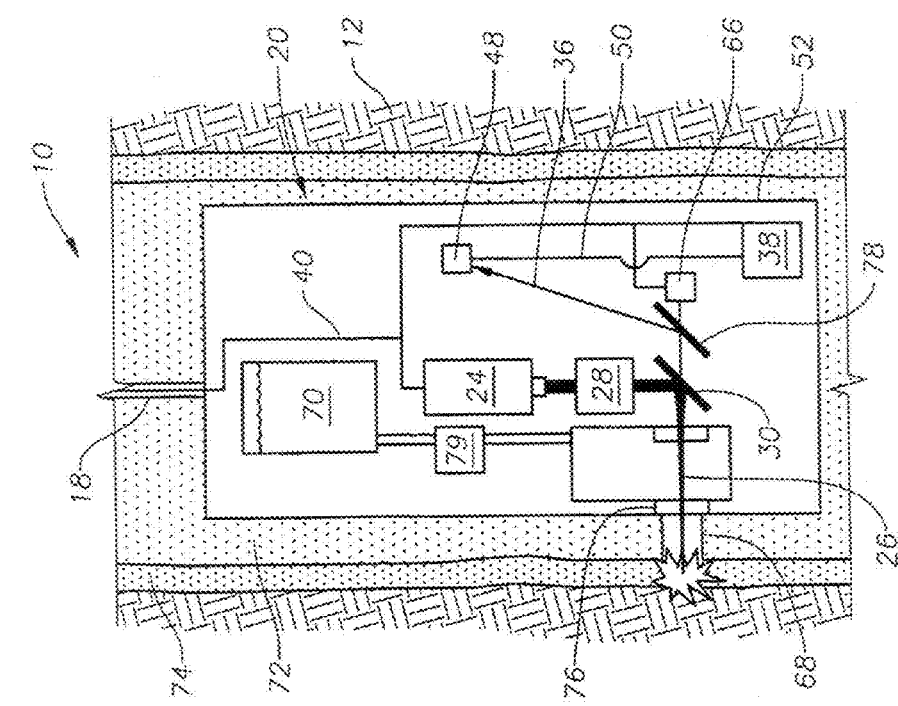

DRILLING, PERFORATING AND FORMATION ANALYSIS

CROSS-REFERENCE TO RELATED APPLICATIONS

This application is a continuation application of and claims priority to U.S. patent application Ser. No. 10/987,923, filed on Nov. 12, 2004 now U.S. Pat. No. 7,490,664.

TECHNICAL FIELD

The present disclosure relates generally to drilling and completing a well in an earth formation, and more specifically, to systems and methods for drilling, perforating, and analyzing the earth formation.

BACKGROUND OF THE INVENTION

Once a well bore has been drilled and one or more zones of interest have been reached, a well casing is run into the well bore and is set in place by injecting cement or other material into the annulus between the casing and the well bore. The casing, cement and formation are then perforated to enable flow of fluid from the formation into the interior of the casing.

In the past, the casing, cement and formation have been perforated using bullets or shaped charges. Both techniques, however, may result in a perforation having a positive skin, i.e. localized decreased permeability that reduces the production of formation fluid from the formation into the perforation. It is generally desirable that the perforations have a neutral or a negative skin, i.e. localized increased permeability resulting in an increased production of formation fluid. In addition, these traditional perforating methods rely on the use of explosives, which pose obvious safety, transportation and security issues.

Known perforating techniques, as well as drilling techniques, do not provide any analysis of the formation rock being perforated or drilled. More so, there is no known technique for analyzing the chemical elements and certain other chemical characteristics of formation rock in situ, that is, without removing the rock from the well. Such analysis would be helpful in determining the optimal location and depth for the current and other perforations, provide in-situ formation evaluation at the perforation site, or on a larger scale, assist in evaluating the current well or other wells. Presently, to obtain an analysis of the formation rock being perforated or drilled, a representative sample of the formation rock must be retrieved to the surface and analyzed. Depending on whether the analysis can be performed on site, such analysis may add days or even weeks to the well completion. Further, the analysis involves material that may have been altered in the process of removing it from the well.

Therefore, there is a need for a system and method of perforating a well bore that enables efficient production from the formation, for example, by producing perforations with a negative skin. It is desirable to accomplish perforating operations without the use of explosives. Furthermore, there is also a need to enable a more immediate analysis of the formation rock being drilled and/or perforated.

SUMMARY OF THE INVENTION

The present disclosure is drawn to a system and method of drilling and/or perforating that uses a laser beam to remove material, such as to perforate the casing, cement and formation. The system and method can further or alternately encompass material analysis that can be performed without removing the material from the well bore. The analysis can be performed apart from or in connection with drilling operations and/or perforating the casing, cement and formation.

In one illustrative implementation, a laser beam device is adapted to output a laser beam. A laser beam directing device is provided that is adapted to direct the laser beam to at least one of remove material or heat material to emit light about a well bore in an earth formation at two or more locations substantially concurrently. In some implementations, the laser beam directing device is adapted to direct the laser beam at the first of the at least two locations in a first duty cycle that is less than one and direct the laser beam to a second of the at least two locations during an off cycle of the first duty cycle. The laser beam directing device can be adapted to be inserted into a well bore and to direct the laser beam into a wall of the well bore. A focusing array can be provided, and the focusing array can be adapted to adjust a focal length of the laser beam longer as a depth of a hole being formed by removing material increases. An extendable light path can be provided, and the extendable light path can be extendable into a hole being formed by removing material. The extendable light path can be adapted to transmit the laser beam and/or light emitted from the material. An emitted light analyzing device can be provided that is adapted to determine at least one chemical characteristic of the material being heated. For example, the analyzing device can determine a chemical element of the material being heated. The emitted light analyzing device can be adapted to perform laser induced breakdown spectroscopy. A fluid outlet can be provided to direct a fluid to at least partially overlap with the laser beam. The outlet can be adapted to direct the fluid to at least partially clean a filter cake from the surface of the well bore. The outlet may also or alternately be adapted to assist in removing debris generated during the perforating or drilling process.

Another illustrative implementation encompasses a method wherein a laser beam is directed at a first location in a well bore in an earth formation in a plurality of first time intervals. The laser beam is adapted to at least one of remove material during the first time intervals and heat material to emit light during the first time intervals. The laser beam is directed at a second location in at least one second time interval intervening the first time intervals. In some implementations, directing the laser beam at a first location in a plurality of first time intervals comprises operating the laser beam continuously and directing the laser beam away from the first location at times other than the first time intervals. The method can further include determining at least one chemical characteristic of the material being heated about at least one of the first and the second location using laser induced break down spectroscopy. Determining the at least one chemical characteristic can be performed substantially concurrently with removing material. A fluid can be directed to at least partially overlap with the laser beam and/or the emitted light. The fluid can be adapted to transmit the laser beam and/or the emitted light. The fluid can be directed to impinge on a surface of the well bore, and can be adapted to at least partially clean the surface of the well bore (including the perforation tunnel).

Another illustrative implementation encompasses an apparatus having a laser beam device adapted to direct a laser beam into a wall of a well bore in an earth formation. The laser beam is adapted to heat material to emit light. A spectroscopy device is provided and adapted to receive the light emitted and determine at least one chemical characteristic.

Another illustrative implementation encompasses a method including heating material within the well bore to cause at least a portion of the material to emit light. At least a portion of the emitted light is received, and at least one chemical characteristic of the material is determined from the emitted light.

Another illustrative implementation encompasses an apparatus for use in analyzing an earth formation defining a well bore when the earth formation within the well bore has been heated to emit light. The apparatus includes an emitted light receiver adapted for insertion into the well bore and adapted to receive the light emitted from the formation. A spectroscopy device is provided and adapted to detect one or more wavelengths and/or a wavelength spectrum of the light emitted from the formation, as well as or alternatively the presence, absence or intensity of one or more wavelengths.

Another illustrative implementation encompasses a method of analyzing an earth formation. According to the method an assembly is inserted into a well bore. The assembly has a material removal device adapted to remove material and an analysis device adapted to determine at least one chemical characteristic of material. Material is removed from the well bore using the material removal device. Without removing the assembly from the well bore, at least one chemical characteristic of the earth formation is determined from light emitted from the formation.

Another illustrative implementation encompasses a device for removing material of an earth formation. The device includes a laser device adapted to output a laser. The laser is adapted to remove material of the earth formation. A laser directing device is provided that is adapted for insertion into a borehole and adapted to direct the laser to remove material of the earth formation in a first area and a second area. The first and second areas may be disparate or contiguous.

Another illustrative implementation encompasses a method of removing material of an earth formation. According to the method a laser is directed into the earth formation in a first trajectory to remove material in a first area. The laser is directed into the earth formation in one or more additional trajectories different from the first trajectory to remove material in one or more additional areas, at least one of which at least partially coincides with the first area.

Another illustrative implementation encompasses an apparatus for insertion into a well bore defined in an earth formation. The apparatus includes a housing and a light. The light path is adapted to displace less optically transmissive material in the well bore and to transmit light at least part way between the housing and the earth formation. In some implementations the light path comprises at least one of a fluid, at least one fiber-optic, or a substantially evacuated passage. The apparatus can further include a laser device adapted to output a laser beam. The apparatus can further include an emitted light receiver adapted to receive light emitted by a heated material. In one implementation the light path can include a fluid and the apparatus can further include a fluid outlet. The fluid outlet is adapted to direct the fluid to at least partially coincide with at least one of the laser beam and the emitted light. The fluid outlet can be adapted to direct the fluid substantially perpendicular to a wall of the well bore. The fluid outlet can be adapted to direct the fluid to substantially clean a surface of the earth formation. The fluid can include at least one of water, oil, and a substantially transparent weighting agent. A fluid reservoir can be positioned at least partially within the housing. A laser used by a laser distance meter can be at least partially transmitted by the light path. The light path may be extendable into a hole being formed in the earth formation. The apparatus can include a tubular snorkel extendable outward from the housing where the light path passes through the tubular snorkel. The tubular snorkel can be adapted to substantially seal with a wall of the well bore. An interior of the tubular snorkel can be substantially evacuated to define the light path. The tubular snorkel can include an elastomeric body that is expanded to extend outward from the housing, for example by being inflated or extruded. The apparatus can include a first seal adapted to seal an annulus between housing and the well bore, a second seal axially offset from the first seal and adapted to seal the annulus between housing and the well bore, and the light path can include a fluid introduced into the annulus between the first and second seals.

Another illustrative implementation encompasses a method of communicating light between a device positioned in a well bore defined in an earth formation and the earth formation. According to the method, less optically transmissive material is displaced with an optically transmissive light path positioned between a housing of the device and the earth formation. Light is transmitted at least part way between the earth formation and the device with the optically transmissive light path. In some implementations the less optically transmissive material may be displaced by at least one of a fluid, at least one fiber-optic, or a substantially evacuated passage. Transmitting light with the optically transmissive light path can include transmitting at least one of a laser beam and light emitted from heated material. A fluid can be directed on a wall of the well bore. The fluid can be directed to clean a surface of the earth formation. The fluid can be directed to remove debris generated in a perforating or drilling process. Displacing less optically transmissive material can include extending a fiber-optic outward from the housing of the device. The fiber-optic may extend into a perforation tunnel as it is being excavated into the earth formation. A tubular snorkel can be extended outward from the housing into the well bore. In this instance, displacing less optically transmissive material can include positioning the light path within the tubular snorkel. The interior of the tubular snorkel can be substantially evacuated to define the light path. Extending the tubular snorkel can include at least one of inflating and extruding an elastomeric body. Displacing less optically transmissive material within the well bore can include actuating a first seal to substantially seal an annulus between housing and the well bore, introducing an optically transmissive fluid between housing and the well bore, and actuating a second seal to substantially seal the annulus between housing and the well bore.

Another illustrative implementation includes a well feedback system. The well feedback system includes an emitted light receiver insertable into a well bore and adapted to receive light emitted from material within the well bore that has been heated to emit light. An emitted light analysis device is provided that is adapted to determine at least one of a chemical and a physical characteristic of the material from the emitted light. A tool for performing a function related to the well is provided. An operation of the tool is adjusted in relation to at least one of the chemical and the physical characteristic determined by the emitted light analysis device. In some implementations the operation adjusted includes at least one of location direction and rate of material removal. The operation can be adjusted to at least one of adjust material removal efficiency and adjust formation exposure. The physical characteristic in some implementations can include one or more of lithology, formation hardness, competency, porosity, permeability, specific heat, thermal conductivity, and thermal diffusivity. The tool can include a laser tool and operation of the laser tool can be adjusted by adjusting at least one of the energy, power, frequency, duty cycle, trajectory and focal point of a laser beam.

Another illustrative implementation is drawn to a method of operating a well tool. According to the method an emitted light is received from material within the well bore that has been heated to emit light. Operation of the well tool is adjusted in relation to the received emitted light. In some implementations the method can further include analyzing the emitted light to determine at least one of a chemical and a physical characteristic of the material. Receiving emitted light and adjusting operation of the well tool can be performed concurrently. In one instance, the well tool is a material removal tool and adjusting operation of the well tool includes adjusting at least one of the location direction or the rate of material removal. Operation of a well tool can be adjusted to at least one of adjust material removal efficiency or adjust formation exposure. In one instance, the well tool is a laser tool adapted to direct the laser beam into a wall of a well bore. In such an instance, adjusting operation of the well tool includes adjusting at least one of the energy, power, frequency, duty cycle, trajectory, and focal point of the laser beam. The laser beam can be adapted to remove material and the operation adjusted to change the material removal mode in relation to the received emitted light. The emitted light can be analyzed to determine at least one of a physical and a chemical characteristic of the material, and the operation adjusted to adjust the determination of the characteristic. In one instance the well tool is a drilling tool, and the adjusting operation of the well tool in relation to the received emitted light includes adjusting drilling operations to drill an additional well bore selected in relation to the emitted light. In another instance the well tool is a drilling tool, and the adjusting operation of the well tool in relation to the received emitted light includes adjusting drilling operation to drill additional well bore, the direction of the additional well bore drilling selected in relation to the emitted light. In one instance the well tool is a perforating tool, and adjusting operation of the well tool in relation to the received emitted light includes adjusting perforating operations to perforate the well bore in additional locations selected in relation to the emitted light. In one instance the well tool is a drilling tool or a perforating tool, and adjusting operation of the well tool in relation to the received emitted light includes adjusting ongoing perforating or drilling operations to adjust the rate or mode of material removal. The rate or mode can be adjusted to optimize material removal.

An advantage of some of the implementations is that they may enable at least one chemical characteristic of an earth formation to be determined without removing the formation or the analysis tool from the well bore. Therefore, chemical analysis can be performed during a single trip of the drilling string, tubing string or wireline into the well bore. Multiple locations (both axially and circumferentially) in the well bore can be analyzed during the same trip. In the case of drilling or perforating, the analysis can be performed without having to remove the drilling or perforating equipment, and the analysis can be performed concurrently with the drilling or perforating processes. Such concurrent analysis enables more frequent sampling of the formation, as well as, more ready use of the formation information in drilling or perforating.

Another advantage of some of the implementations is that material can be removed or analyzed in two or more locations substantially concurrently.

Another advantage of some of the implementations is that material can be removed or heated in specified patterns, for example, circumferential grooves or conical perforations.

Another advantage of some of the implementations is that increased permeability (negative skin) develops in the formation in the area of the material removed.

Another advantage of some of the implementations is that perforations may be made without the use of explosives.

BRIEF DESCRIPTION OF DRAWINGS

FIG. 10 is a side cross-sectional view of another illustrative laser tool constructed in accordance with the invention including provisions for a fluid-based light path;

FIG. 11 is a side cross-sectional view of another illustrative laser tool constructed in accordance with the invention including provisions for a fluid-based light path and having stabilizer fins;

DETAILED DESCRIPTION OF THE PREFERRED EMBODIMENTS

Figure 1:
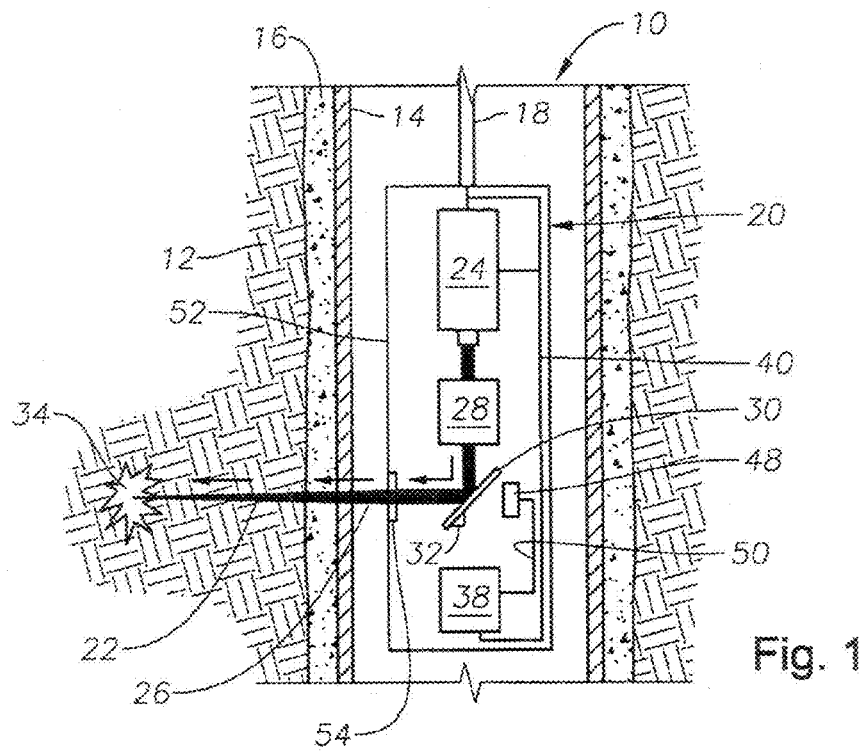
FIG. 1 is a side cross-sectional view of an illustrative laser tool constructed in accordance with the invention depending from a wireline and depicted perforating a well bore.
Figure 2:
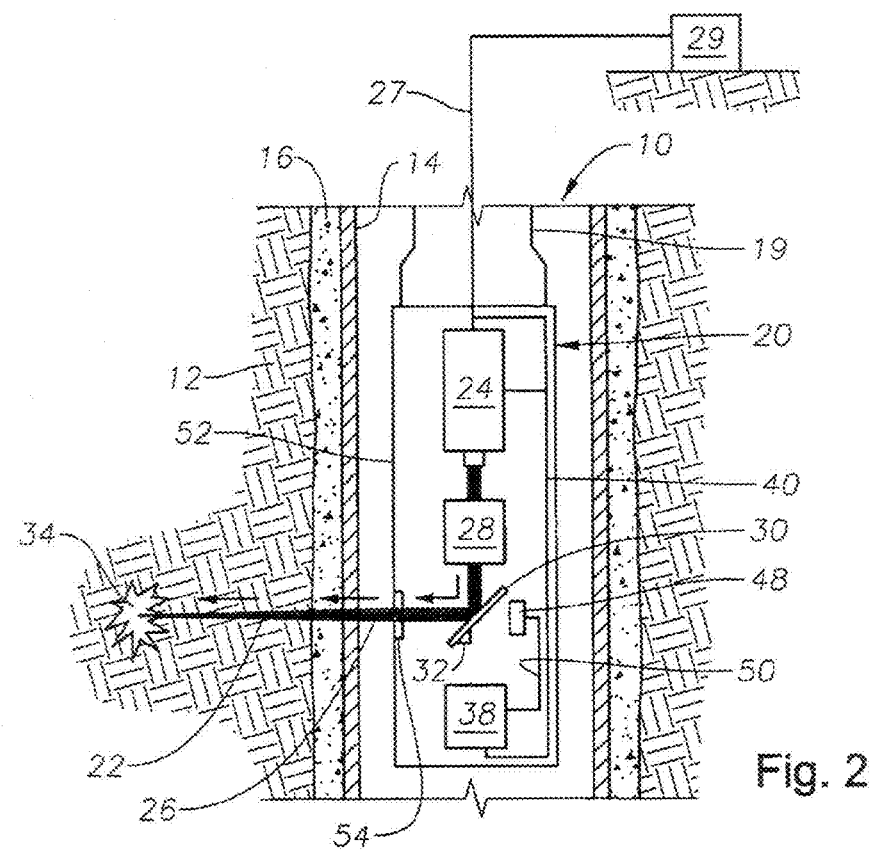
FIG. 2 is a side cross-sectional view of an alternate illustrative laser tool constructed in accordance with the invention depending from a tubing string and depicted perforating a well bore.

Referring to FIGS. 1 and 2, a cased well bore 10 in a formation 12 has a casing 14 affixed therein. A layer of cement or similar material 16 fills an annulus between the casing 14 and the well bore 10. An illustrative laser tool 20 constructed in accordance with the invention is depicted in use perforating the well bore 10. The illustrative laser tool 20 is adapted to be inserted into the well bore 10 depending from a wireline 18 (FIG. 1) or a tubing string 19 (FIG. 2), and direct a laser beam 26. Although depicted as removing material from the formation 12 to form a perforation 22, the laser tool 20 can be adapted to also or alternatively drill a new well bore, extend an existing well bore, or heat material to emit light for use in laser induced breakdown spectroscopy (LIBS). As the illustrative laser tool 20 of FIGS. 1 and 2 is depicted perforating a cased well bore 10, it is directing the laser beam 26 onto the casing 14, the cement 16 and the formation 12. The illustrative laser tool 20 and related concepts described herein are equally applicable to an "open hole" well bore as depicted in FIGS. 10-11. An open hole well bore is one in which at least a portion of the well bore has no casing. Furthermore, the laser tool 20 may be used in perforating or drilling through various equipment installed in a well bore, and is not limited to perforating through casing, cement layers, and formation. When referring to a wall of a well bore herein, the wall can include any interior surface in the well bore, such as a sidewall or end/bottom wall thereof.

Power and/or signals may be communicated between the surface and the laser tool 20. Wireline 18 may include one or more electrical conductors which may convey electrical power and/or communication signals. Wireline 18 may additionally or alternatively include one or more optical fibers which may convey light (e.g. laser) power, optical spectra, and/or optical communication signals. Neither the communication of power, nor signals to/from the surface, are necessary for the operation of the implementations. In lieu of such communication downhole batteries and/or downhole generators may be used to supply the laser tool 20 power. A downhole processor may be employed to control the laser tool 20, with relatively little (as compared to wireline) or no communication from the surface. For example, instructions for performing operations may be preprogrammed into the processor (ex. processor 44 in FIG. 4) before running the laser tool 20 into the well bore 10 and/or the laser tool 20 may respond to simple commands conveyed via surface operations such as rotary on/off, relatively low data rate mud-pulse, electromagnetic telemetry, and acoustic telemetry communication.

In implementations incorporating a tubing string 19, the tubing may be continuous tubing or jointed pipe and may be a drilling string. The tubing string 19 may incorporate a wireline 18 as described above. Tubing string 19 may be "wired drill pipe," i.e. a tubing having communication and power pathways incorporated therein, such as the wired drill pipe sold under the trademark Intellipipe by Grant Prideco, Inc. The tubing string 19 may contain a smaller tubing string within for conveying fluids such as those used in the fluid based light path described below or for conveying chemicals used by the laser.

As discussed above, the laser tool 20 may be configured for use in analyzing material using laser-induced breakdown spectroscopy (LIBS). In LIBS, at least a portion of the material being sampled is heated, for example to a plasma or an incandescent state, and the wavelength spectrum and intensity of the light it emits is measured to determine a chemical characteristic of the material, for example, the chemical elements of the material. The light may be in either or both of the visible and invisible spectrums. The laser tool 20 can also be configured to determine a physical characteristic of the material, such as its temperature or thermal properties. The laser tool 20 can operate to heat the rock of the formation 12 (or other material being analyzed) in situ, i.e. without removing the rock of the formation 12, using laser beam 26 while the laser tool 20 is operating to remove material (drilling or perforating) or apart from operation of the laser tool 20 to remove material. In an instance where the laser tool 20 is not operated to remove material or is not configured to remove material, it may be desirable to incorporate the laser tool 20 into a tubing string 19 having an alternate material removal device 91 (see FIG. 11), such as a drilling bit or bullet or shaped charge perforating tool.

Figure 3:
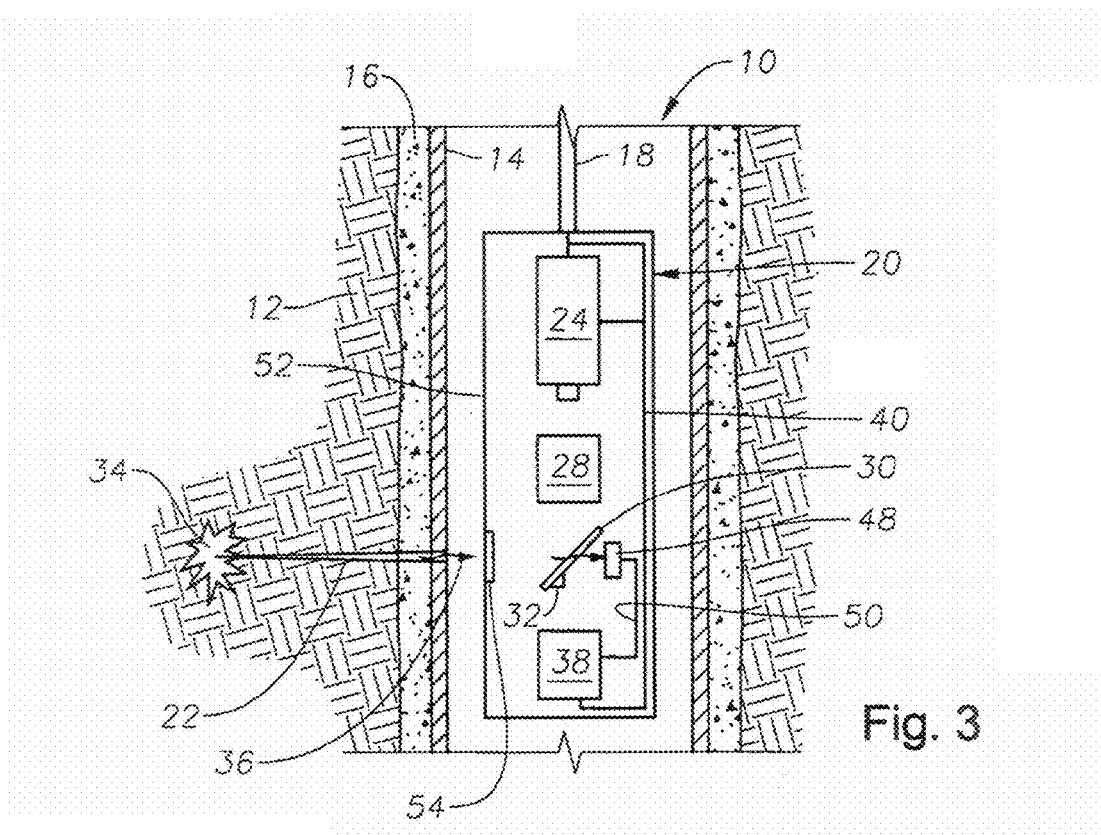
FIG. 3 is the illustrative wireline laser tool of FIG. 1 depicted receiving emitted light in accordance with the invention.

FIG. 3 depicts area 34, the portion of the formation 12 heated by the laser beam 26, emitting light 36 (represented by the wavy arrows). The portion of the formation 12 being heated is depicted relatively deep within the formation (in the radial direction) in relation to the well bore 10, but it is understood that this could be at any particular radial depth, e.g. at the borehole interior surface, at a mud cake surface, at a casing surface, within a cement sheath, or at a location within the formation. Some of the emitted light 36 will travel in the direction of the arrows back through the formation 12 and to the laser tool 20. The laser tool 20 can be provided with an emitted light receiver 38 to receive the emitted light 36 from the formation 12. The emitted light receiver 38 is adapted to receive emitted light 36 and perform one or more of the following: transmit the emitted light 36 to the surface; detect a characteristic of the emitted light 36 (ex. the wavelength spectrum, a portion of the wavelength spectrum, and/or a power or intensity level of the emitted light 36) and log or transmit a signal representative of the detected characteristic to the surface; and detect a characteristic of the emitted light 36, determine one or more chemical characteristics of formation 12 from the light characteristics and log or transmit a signal representative of the chemical characteristics to the surface. In an embodiment where the emitted light 36 or signal representative of the emitted light 36 characteristics are transmitted to the surface, a determination of the chemical characteristics of the formation 12 can be determined by a computer remote from the laser tool 20, for example at the well site or remote from the well site.

The laser tool 20 can control the timing, direction, focus and power of the laser beam 26. Different light patterns can be applied by varying the timing (i.e. pulsing), direction, focus, and power of the laser beam 26 depending on the type of materials to be removed or analyzed, for example, the casing 14, the cement 16 and different types of rock in the formation 12. Accordingly, in removing material, the laser beam 26 light patterns can be adjusted to crack, spall, melt or vaporize the materials to be removed and change as the material type changes. The laser beam 26 can be configured to remove material in a single continuous pulse or multiple pulses. The multiple pulses may be cyclical, such as in a duty cycle. The power of the laser beam 26 can be selected such that the duty cycle necessary to remove the material in the desired manner (crack, spall, melt or vaporize) is less than 100%. In most instances of removing material during perforating operations, the laser beam 26 is directed on the formation with a duty cycle that causes the rock to chip or spall.

The laser beam 26 can be configured to heat the material being analyzed to a plasma or incandescent state in a single pulse, a continuous pulse or multiple pulses. The multiple pulses may be cyclical, such as in a duty cycle. The power of the laser beam 26 used in analyzing material can be selected such that the duty cycle necessary to heat the material being analyzed to a plasma or incandescent state is less than 100%.

If configured to both remove and analyze material, the laser tool 20 can be configured to remove material and heat the material being removed or the remaining material to emit light 36 during the same duty cycle or during separate cycles. For example, the laser tool 20 can remove material during a first duty cycle and operate to heat material, at the same location or a different location, in a second duty cycle.

The power of the laser beam 26 can be equal from cycle to cycle, vary from cycle to cycle, or the laser beam can be fired in non-cyclical pulses of varying power. For example, it may be desirable to use a multi-pulse technique to heat the formation 12 to enable use of a lower powered laser than is necessary to heat the formation in a single pulse. In a multi-pulse technique, a first laser beam pulse is fired toward the material being analyzed to generate a cavity in the material and/or the interceding or surrounding materials, such as well fluids and drilling mud, resulting from rapidly expanding vaporized material. A second, higher power pulse is then fired into the material being analyzed to heat the material to a plasma or incandescent state. The multi-pulse technique may also encompass firing the first laser beam in a higher power pulse than the second laser beam pulse (e.g. for blasting way interceding material). Additional laser beam pulses may be fired, of higher or lower power than the first and second laser beam pulses, as is desired. For example, a third laser beam pulse may be fired to perforate the formation rock.

As a heated portion of the formation may continue to emit light for a brief period of time after the laser beam has ceased being directed at the location, the emitted light receiver 38 can be operated to receive emitted light 36 either (or both) while the laser beam 26 is being directed at the location and afterwards, for example during an off cycle of the laser beam 26 or while the laser beam 26 is being directed to heat or remove material in a different location. It is also within the scope of the invention to re-heat the formation at some time after the laser tool 20 has been operated to remove material at the location, and thereafter use the emitted light receiver 38 to receive the emitted light 36.

In FIGS. 1 and 2, the illustrative laser tool 20 includes a laser beam device 24 that generates or relays a laser beam 26 into the formation 12. The laser tool 20 may optionally be provided with a focusing array 28 through which the laser beam 26 passes. The laser beam device 24 may generate the laser beam 26, and thus may be an electrical, electro-chemical laser or chemical laser, such as a diode laser or an excimer or pulsed Na:YAG laser, dye laser, CO laser, $CO_2$ laser, fiber laser, chemical oxygen iodine laser (COIL), or electric discharge oxygen iodine laser (DOIL). The laser beam device 24 may relay the laser beam 26 generated remotely from the laser tool 20, such as a laser generated by a laser generator 29 on the surface and input into the laser beam device 24 via a transmission line 27 (FIG. 2), such as an optical fiber or light path. In some implementations it may be desirable to use a DOIL to increase service intervals of the laser tool 20, because a DOIL does not substantially consume the chemicals used in creating the laser beam and the chemicals need not be replenished for an extended duration. It is to be understood that the examples of particular lasers disclosed herein are for illustrative purposes and not meant to limit the scope of the invention.

The laser beam may be pulsed, cycled, or modulated by pulsing, cycling, or modulating the control signal, and/or using an optical chopper, shutter, digital micro-mirror device, Kerr cell, or other mechanical, electrical, or photonics based light switching device to shutter, pulse, cycle, or modulate the emitted beam. In some implementations, the laser pulse duration may be on the order of 10 nanoseconds. A Kerr cell is one electro-optical device that may be used to provide shuttering on the order of such speeds.

The focusing array 28 may include one or more optical elements or lenses configured to focus the laser beam 26 at a given focal length or adjustably focus the laser beam 26 to various focal lengths. Some examples of suitable devices for an adjustable focusing array 28 can include one or more electro-optic lenses that change focal length as a function of voltage applied across the lens or one or more fixed lenses and/or mirrors movable to change the focal length. It is understood that there are many suitable devices for manipulating an optical beam which can be actively manipulated, responding to mechanical, acoustical, thermal, electrical or other forms of input energy and numerous such devices are within the scope of the invention. The focusing array 28 focuses the laser beam 26 on the material being removed or heated.

Use of an adjustable focusing array 28 enables the laser beam 26 to be more precisely focused on the material being removed or heated than a fixed focusing array 28, for example, when there is movement of the laser tool 26 relative to the formation 12. An adjustable focusing array 28 also enables the laser beam 26 to be focused on the end wall of the material being removed as the end wall moves deeper into the formation. In removing material, the laser beam 26 can be first focused on the closest surface of the material to be removed then adjusted to maintain focus as the surface from which material is being removed moves deeper into the material. In the case of perforating a well bore 10, the laser beam 26 can be first focused on the interior of the casing 14 and adjusted to maintain focus at an end wall of the perforation 22 as the perforation deepens through the casing 14, the cement 16 and into the formation 12. In heating a material being analyzed to emit light, the laser beam 26 can be focused on the material being analyzed. The focal length and/or properties of the laser beam may be actively manipulated, for example to compensate for movement of the laser tool 20 relative to the material being heated or removed.

A length to the desired location can be determined using a distance meter 66 (FIG. 10), such as an acoustic or optical distance meter, configured to measure a distance between the laser tool 20 and the material being removed or analyzed. That length can then be used in determining a focal length at which to focus the adjustable focusing array 28. Optical distance meter (or range finding) technologies are known, for example using a laser beam and a photo diode to detect the light returned from the formation whose range is of interest wherein a modelable relationship exists between the distance to be measured, the focal point of the laser beam, and the intensity of the returns. By varying the focal point of the beam and monitoring the intensity of the returns, the distance to the formation may be inferred. Alternatively, a distance, relative distance, or change in distance may be inferred with a single focal point by correlating intensity to a model or experimental data, or monitoring intensity decrease or increase at different times during a process (e.g. the perforating) expected to result in a change in such distance. As another alternative, optical time domain reflectometry may be employed as is known to measure the time a flight of a pulse of light to and from the formation, from which distance may be determined. The laser beam used by the optical distance meter 66 may be from a laser beam device 24 used for removing or heating material, or maybe a separate beam from a separate device, such as the distance meter 66 itself.

Figure 12:
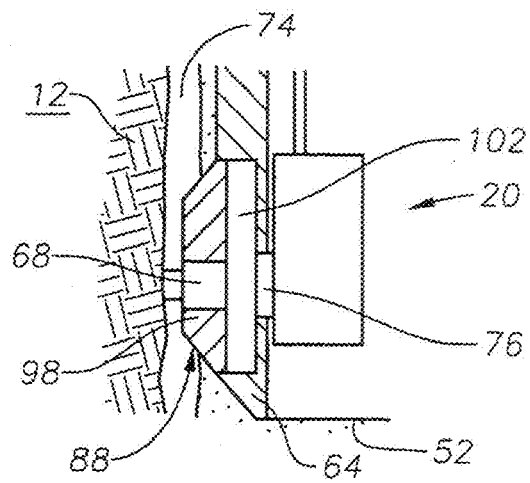
FIG. 12 is a detail side cross-sectional view of another illustrative laser tool constructed in accordance with the invention including provisions for an extendable snorkel shown extending from a stabilizer.

When using a fixed focusing array 28, constraining the relative tool/formation movement so that the distance from the well bore 10 wall to the fixed focusing array 28 remains fixed in relation to the focusing array's focal length ensures that the laser beam 26 will maintain the desired focus. In an adjustable focusing array 28, it may be desirable to constrain relative tool/formation movement to reduce the magnitude of focal length adjustments necessary to maintain focus. Relative laser tool/formation movement can be reduced by sizing the exterior of the laser tool 20 close to the diameter of the well bore 10 or by providing the laser tool 20 with one or more stabilizer fins 64 as depicted in FIG. 11 that project to a diameter that is close to the diameter of the well bore 10. Movement of the laser tool 20 relative to the formation can be further reduced by providing one or more extendable stabilizers 88, as depicted in FIG. 12, that can be selectively expanded to reside close to or in contact with the wall of the well bore 10. FIG. 12 depicts an extendable stabilizer 88 including a movable stabilizer blade or fin 98 received in a recess 102 of stabilizer 64, and configured to telescope outward into contact with the well bore 10 wall. In a retracted position, the movable stabilizer body 98 is received at least partially within the recess. If a fixed focusing array 28 is used, or if no focusing array 28 is provided, the position of the laser tool 20 within the well bore 10 can be deliberately adjusted to adjust the location of focus of the laser beam 26. In other words, moving the laser tool 20 a given distance in a specified direction will move the focus a similar amount in the direction. In one instance, the position of the laser tool 20 can be adjusted adjusting the movable stabilizer fins 98 to bias the laser tool 20 in the desired direction.

Although the laser beam device 24 can be oriented to fire directly towards the material being removed or heated in one or more trajectories, the illustrative laser tool 20 is configured with the laser beam device 24 firing into a reflector 30. The reflector 30 directs the laser beam 26 toward the formation 12 and may be operated to assist in focusing the laser beam 26 or operate alone in (when no focusing array 28 is provided) focusing the laser beam 26 into the material being removed. In the illustrative laser tool 20 of FIGS. 1 and 2, the laser beam 26 is directed substantially longitudinally through the laser tool 20 and the reflector 30 directs the laser beam 26 substantially laterally into the well bore 10. The laser tool 20 can be configured to fire the laser beam 26 in other directions, for example, down.

The laser beam 26 may be directed to remove material or heat various points around the well bore 10 and in varying patterns. In an illustrative laser tool 20 having a reflector 30, the reflector 30 can be movable in one or more directions of movement by a remotely controlled servo 32 to control the direction, i.e. trajectory, of the reflected laser beam 26. In a laser tool where the laser beam device 24 fires directly into the formation 12 or in a laser tool having a reflector 30, the laser beam device 24 can be movable by control servo to control the trajectory of the laser. In lieu of or in combination with a reflector 30, the laser beam can be directed into the formation 12 using a light path (see FIGS. 5D and 7-9, discussed below), such as a fiber optic, that may optionally be movable by control servo to control the trajectory of the laser beam. The light path may include multiple paths, such as a fiber optic array, that each direct the laser beam in a different trajectory. The multiple paths can be used selectively, individually or in multiples, to direct the laser beam in different trajectories.

Figure 5A:
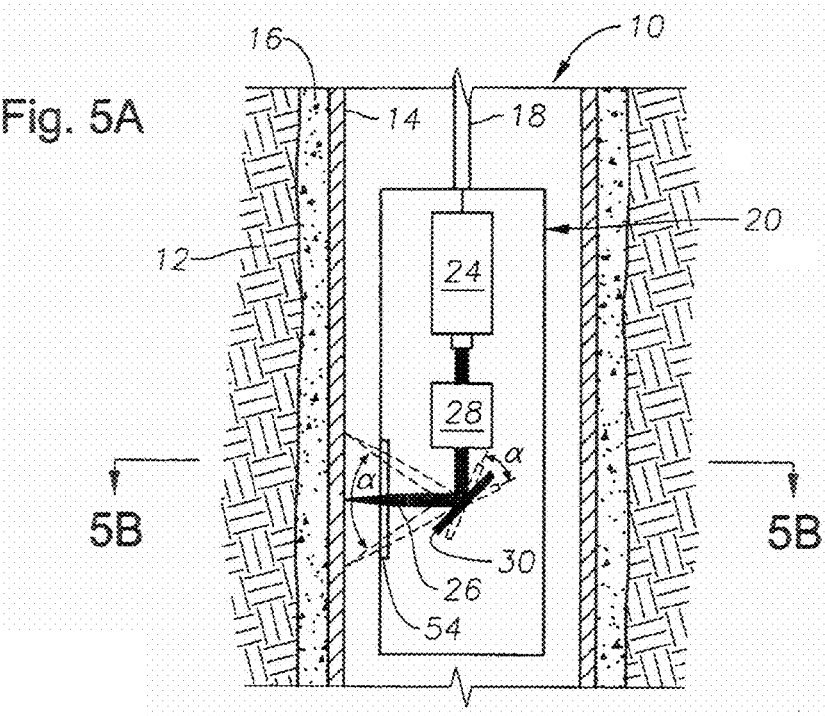
FIG. 5A is a side cross-sectional view of the illustrative laser tool of FIG. 1 showing different trajectories of the laser beam.
Figure 5B:
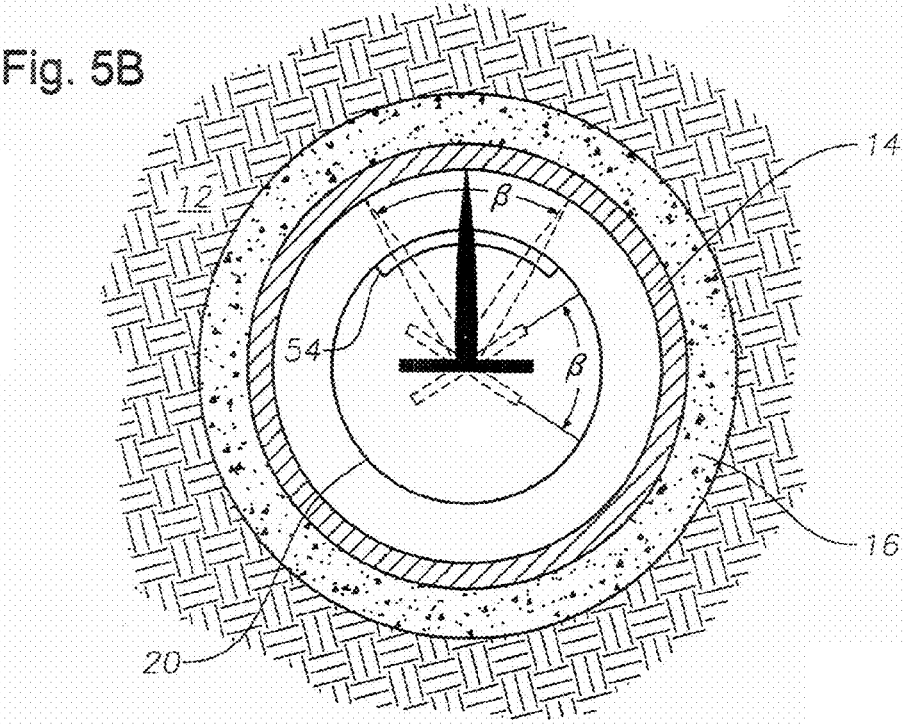
FIG. 5B is a cross-sectional view of FIG. 5A along section line B-B showing different trajectories of the laser beam.
Figure 5C:
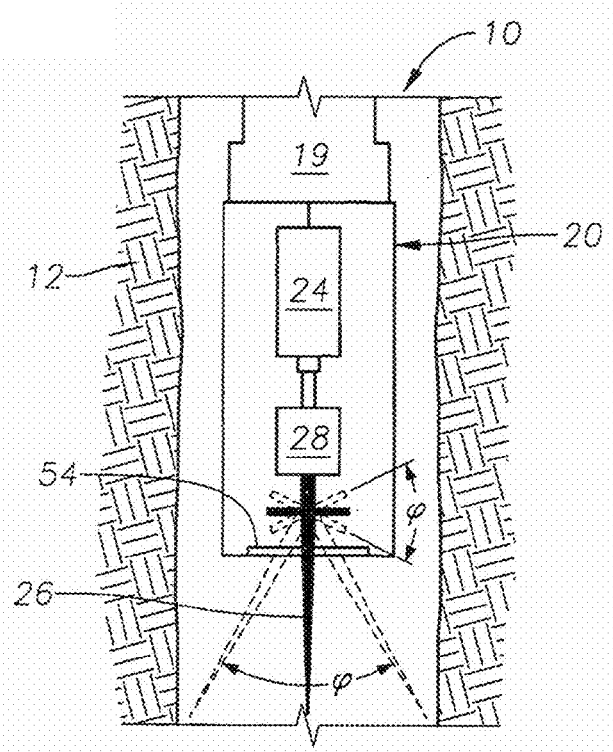
FIG. 5C is a cross-sectional view of an alternate illustrative laser tool showing different trajectories of the laser beam typical in drilling a vertical well bore.

In the illustrative example of FIGS. 1 and 2, the laser beam 26 is directed using the reflector 30 and control servo 32, rather than or in combination with moving the laser tool 20. The control servo 32 can be configured to move the reflector 30, at least one of, about a longitudinal axis of the well bore 10 (see FIG. 5A), about a transverse axis of the well bore 10 (see FIG. 5B), or along at least one of the longitudinal and transverse axis of the well bore 10. FIG. 5A depicts the laser tool 20 firing the laser beam 26 through angle α about the well bore longitudinal axis. Depending on the application, it may be desirable to configure the laser tool 20 so that angle α may be as much as 360°. FIG. 5B depicts the laser tool 20 firing the laser beam 26 through angle β about the well bore transverse axis. Depending on the application, it may be desirable to configure the laser tool 20 so that angle β may be as much as 360°. The laser tool 20 can be appropriately configured so as not to fire the laser beam 26 upon itself. FIG. 5C depicts an illustrative laser tool 20 firing in multiple trajectories, through angle φ, typical for drilling a vertical well bore 10. Depending on the application, angle φ may be as much as 360° and may be oriented through 360° polar about the longitudinal axis of the laser tool 20.

Figure 5D:
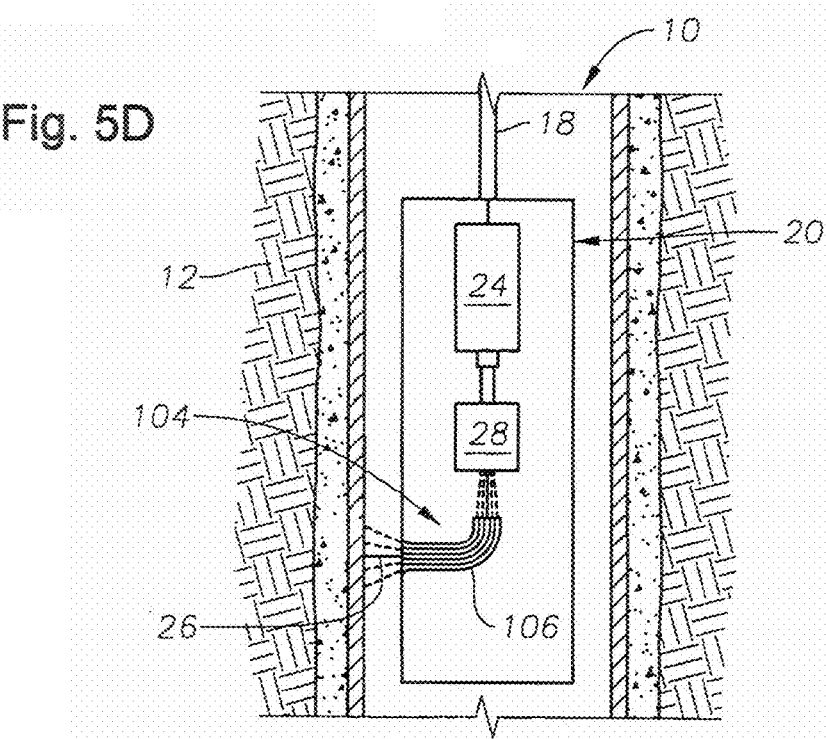
FIG. 5D is a cross-section view of another alternate illustrative laser tool showing different trajectories of the laser beam achieved using a fiber optic array.
Figure 6:
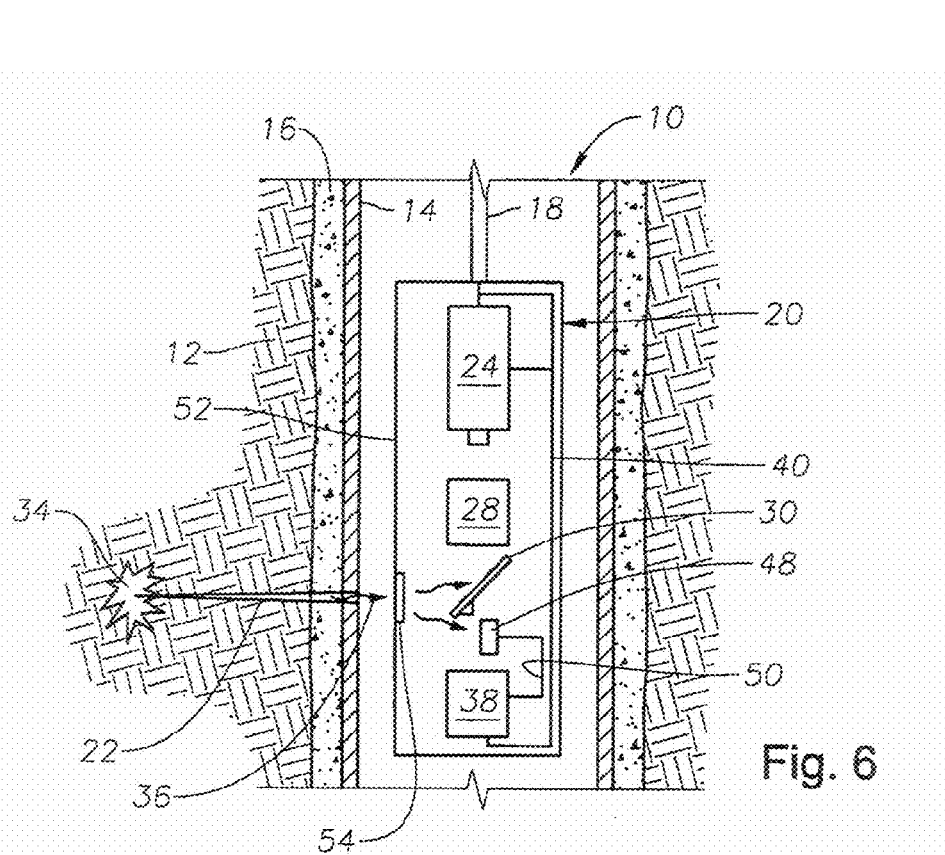
FIG. 6 is a side cross-sectional view of an alternate illustrative laser tool constructed in accordance with the invention and depicted receiving emitted light from the formation.

FIG. 5D depicts a illustrative laser tool 20 that uses a light path 104 comprised of multiple optical fibers 106 each oriented to fire in a different trajectory. The laser beam 26 may be directed through all of the multiple optical fibers 106 substantially simultaneously, or may be multiplexed through the multiple optical fibers 106, for example, as a function of duty cycle as is described below. Likewise, emitted light can be received through the multiple optical fibers 106 for use in material analysis as is described herein. Although depicted with a specified number of optical fibers 106 arranged vertically, the number and pattern of the optical fibers 106 can vary. For example, only one optical fiber 106 can be provided. In another example, the pattern in which the optical fibers 106 are arranged can additional or alternatively extend circumferentially about the laser tool 20 to reach circumferential positions about the well bore 10. The arrangement of optical fibers 106 can be configured to produce specified patterns in the material removed, heated, and/or analyzed.

By directing the laser beam 26 relative to the laser tool 20, with reflector 30, light path 104, or otherwise, the laser tool 20 can remain in a single position (without further adjustments or reorientation) and remove or heat material in multiple locations around the well bore 10. Accordingly, the number of adjustments and/or orientations of the laser tool 20 during an entire operation is reduced. Physically moving the laser tool 20 is time-consuming relative to adjustment of the laser trajectory using the configurations described herein (ex. by moving reflector 30). Therefore, the ability to reach multiple trajectories without moving the laser tool 20 reduces the amount of time necessary to perform operations (drilling, perforating, formation analysis).

According to the concepts described herein, the laser beam 26 can be manipulated with multiple degrees of freedom and focal points to remove material in many different patterns. So for example, a slice or thin wedge can be removed from the wall of the well bore 10, orthogonal to and along the length of the well bore 10, and orthogonal to a formation bedding plane, with a larger thickness at its distal end from the well bore 10, and exposing far more formation surface than traditional perforating operations. The concepts described herein enable a perforation hole to be shaped (such as by providing slots, rather than tubes or pits) to minimize fluid pressure down-draw. Multiple shapes can be envisioned within the implementations which may promote hydrocarbon recovery rate, total recovery and efficiency.

In the illustrative laser tool 20, the laser beam 26 can be directed to remove or heat material circumferentially about the well bore 10 by actuating the control servo 32 to rotate the reflector 30 about a longitudinal axis of the well bore 10 and/or actuating the reflector 30 to move along the transverse axis of the well bore 10. The laser beam 26 can be directed to remove or heat material along the axis of the well bore 10 by actuating the control servo 32 to rotate the reflector 30 about a transverse axis of the well bore 10 or move along the longitudinal axis of the well bore 10. The laser beam 26 can be directed to remove or heat material in an area that is larger than could be removed in a single trajectory, by actuating the reflector 30 to rotate about and/or translate along at least two axes, for example the longitudinal and transverse axis. The laser beam 26 would then be directed in two or more different trajectories to substantially adjacent locations on the material being heated or removed. For example, by directing the laser beam 26 to project on the material being removed or heated at quadrants of a circle, the laser beam 26 can substantially remove or heat the material in a circular shape. By directing the laser beam 26 in two or more trajectories at the same location, the laser tool 20 can remove material to form a conical perforation having a largest diameter at the opening or having a smallest diameter at the opening. Also, the laser beam 26 may be directed in one or more trajectories to form a perforation in the earth formation, and concurrently while forming the perforation or subsequently, be directed in one or more trajectories to widen the perforation. The laser beam 26 can also be directed in two or more different trajectories to remove or heat material of the earth formation in a substantially continuous area or two or more disparate areas.

The laser being directable can be also be use to drill more efficiently and/or with unique hole characteristics, as compared to both the classic drill-bit drilling and prior non-directable laser drilling. In drilling with the laser beam 26, the laser beam 26 would be directed axially rather than radially, and the laser beam tool 20 would be conveyed on the bottom of the bottom hole assembly in place of the drilling bit (see FIG. 5C). A circular path could be swept by the laser beam 26, cutting (for example by spalling) a thin annular hole, approximately equal to a desired hole diameter. The resulting "core" sticking up in the middle would be periodically broken off and reverse circulated up the well bore 10, for example up the middle of the drill string 19, to the surface. Accordingly, the laser energy is being used only to cut a small amount of rock (i.e. the annular hole). The same laser beam 26 directing configurations discussed above in the context of perforating could be applied to drilling. Because the material removal is not resulting from a mechanical bit being rotated, a circular cross-section hole is not necessary. For example, the laser beam 26 could be directed to sweep out elliptical, square, or other hole shapes of interest.

Using the directionality of the material removal allows formation of a specified hole or perforation section shape designed and executed for purposes of enhanced production. For example the hole or perforation can be formed in a rectangular, oval, elliptical, or other hole section with a longer axis aligned to expose greater (as compared to a circular cross-section) amount of the producing formation, or aligned to provide greater exposure to an axis of preferred permeability, or preferential production (or non-production) of oil, water, gas, or sand. Such specified hole or perforation section shape may be designed and executed for purposes of well bore or perforation stability, for example a rectangular, oval, or elliptical shape being employed with a longer axis aligned with the principal stress field, for increased stability and reduced tendency of collapse as compared to a circular cross-section.

The power of the laser beam 26 can be selected such that the duty cycle necessary to remove the material in the desired manner (crack, chip, spall, melt or vaporize) and/or heat the material to emit light allows enough time during off cycles of a given trajectory for the laser beam 26 to be directed in one or more additional trajectories. In other words, if the duty cycle necessary to remove and/or heat the material in the desired manner is 10%, the 90% off cycle can be utilized by re-directing the laser beam 26 to remove and/or heat material from one or more additional positions in the well bore 10. The duty cycle for the various positions can be substantially equal or one or more of the positions can have a different duty cycle. For example, the various positions may have a different duty cycle if one or more of the positions are a different material, if it is desired to remove material at a different rate in different positions, or if it is desired to remove material in one or more positions and merely heat material in one or more different positions to emit light. The laser beam 26 can be cycled or pulsed to achieve the required duty cycle or the laser beam 26 can be continuous and moved from position to position to achieve the duty cycle for each respective position. In either manner, the laser tool 20 operates to multiplex removal of material in one or more positions, for example to form one or more perforations 22, substantially concurrently. Likewise if it is desired to drill or perforate a hole that is larger than the laser beam 26 can form on a single trajectory or that otherwise must be formed with two or more trajectories, the same multiplexing technique can be used to remove material in the two or more trajectories substantially concurrently. More so, one or more positions on the earth formation can be heated to emit light substantially concurrently using this multiplexing technique.

Figure 4:
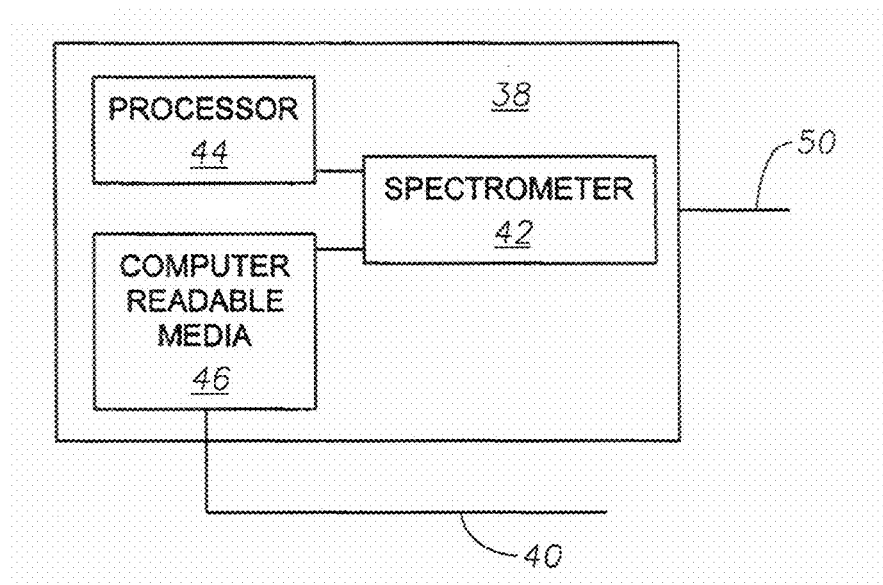
FIG. 4 is a schematic of an illustrative emitted light receiver in accordance with the invention.

In a laser tool 20 configured to analyze material, the emitted light receiver 38 is provided to receive emitted light 36 from the formation 12. In an embodiment that communicates with the surface, the emitted light receiver 38 is coupled to the surface by a communication link 40. The communication link 40 can be a fiber optic or light path for communicating data or light to the surface or can be an electrical or other type of link. The communication link 40 can be used to transmit wavelength spectra or signals indicative of wavelength spectra to the surface for analysis (ex. analysis using a surface based spectrometer and processor for determining the chemical characteristics of the material being analyzed). In an embodiment where the emitted light receiver 38 determines the wavelength spectrum of the emitted light 36, the emitted light receiver 38 can include a pyrometer and/or spectrometer 42 (FIG. 4). In addition to the spectrometer 42, if the emitted light receiver 38 is configured to determine the chemical characteristics of the formation 12 (i.e. perform the LIBS), the emitted light receiver 38 includes at least one processor 44. The emitted light receiver 38 may contain memory or other computer readable media (hereinafter computer readable media 46) for logging the emitted light 36 wavelength spectrum information, logging the chemical and/or thermal characteristic information, and/or storing instructions for the processor 44 to operate at least a portion of the method of operation described herein.

In the illustrative embodiment of FIGS. 1-3, the reflector 30 is dichroic and configured to reflect the wavelength spectrum of laser beam 26 while passing other wavelengths. The laser beam device 24 is configured to emit a laser beam 26 in a wavelength spectrum that is different than the expected wavelength spectrum of the emitted light 36. The emitted light receiver 38 is thus configured to receive the emitted light 36 that passes through the reflector 30. To wit, a lens assembly 48 is provided behind the reflector 30 axially aligned with the incoming emitted light 36 and adapted to focus the emitted light 36 into a transmission path 50, such as a fiber optic, to the emitted light receiver 38. The lens assembly 48 can include one or more lenses, and optionally a filter, as is desired to condition the emitted light 36 before transmitting to the emitted light receiver 38. Alternatively, the emitted light receiver 38 can be configured to receive the emitted light 36 from a position adjacent the laser beam 26. In such an embodiment, the reflector 30 need not be dichroic, and the lens assembly 48 has a filter configured to filter out the wavelength spectrum of the laser beam 26.

Some or all of the components of the laser tool 20 can be encased in a housing 52. The housing 52 has one or more windows 54 adapted to allow passage of the laser beam 26 out of the housing 52 and emitted light 36 into the housing 52. The size and shape of the windows 54 accommodate the aiming capabilities of the laser beam 26 and receipt of emitted light 36. The windows 54 are further adapted to withstand the elevated pressures and temperatures experienced in the well bore 10. Some examples of materials for constructing the windows 54 may be silica, sapphire; or numerous other materials of appropriate optical and strength properties. The windows 54 may have anti-reflection coatings applied to one or both surfaces to maximize the transmission of optical power therethrough while minimizing reflections. The windows 54 may comprise a plurality of optical fibers positioned to direct the laser beam 26 or collect emitted light 36 from multiple locations about the well bore 10, for example the optical fibers may be fanned radially about the laser tool 20.

FIGS. 10 and 11 depict a space conservative manner of locating the laser device 24, the emitted light receiver 38 and a laser based distance meter 66 within the laser tool 20. As described above, the laser device 24 can be configured to fire into a dichroic reflector 30 adapted to reflect the laser beam 26 into the material being removed or heated and pass emitted light 36. A second dichroic reflector 78 can be provided to reflect the emitted light 36 passed by the first dichroic reflector 30 to a lens assembly 48 displaced from the axis of the laser beam 26. By providing both the first and second dichroic reflectors 30 and 78 to be adapted to pass the laser from the distance meter 66, the laser distance meter 66 can then be placed in the axis of the laser beam 26. Additional reflectors can be provided, as is desired, to position the laser distance meter 66 displaced from the axis of the laser beam 26.

Figure 7:
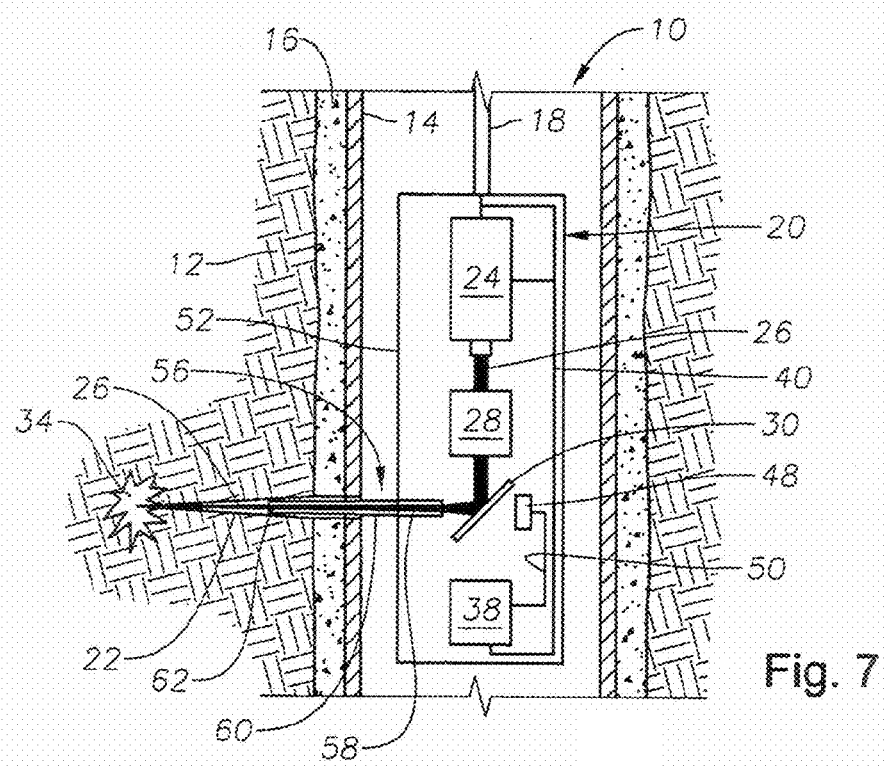
FIG. 7 is a side cross-sectional view of an alternate illustrative laser tool constructed in accordance with the invention having an extendable light path and depicted perforating a well bore.
Figure 8:
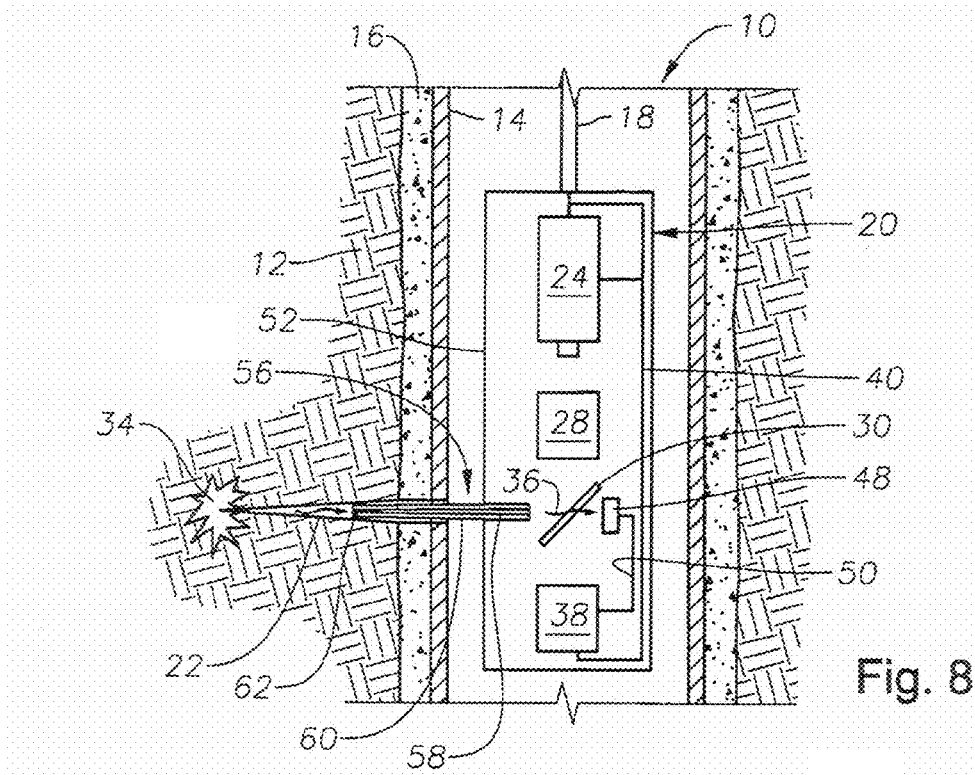
FIG. 8 is a side cross-sectional view of the illustrative laser tool of FIG. 7 depicted receiving emitted light from the formation.
Figure 9:
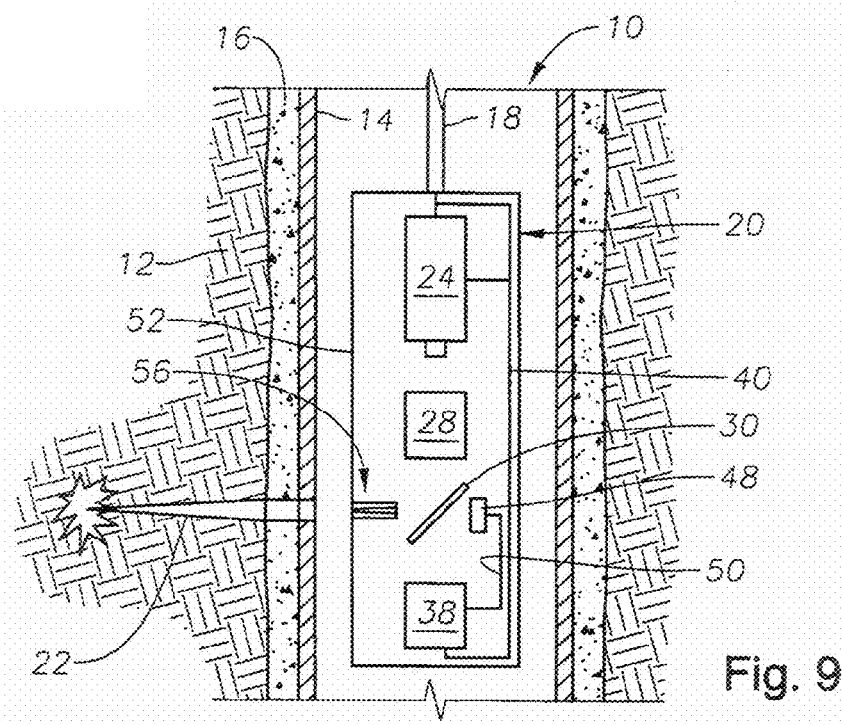
FIG. 9 is a side cross-sectional view of the illustrative laser tool of FIG. 7 depicted with the extendable light path retracted.

The laser tool 20, as depicted in FIGS. 7-9, can include an extendable light path 56 that can be retracted into or extended out from the laser tool 20 and into the perforation 22 (or hole) as it is being formed. While a single light path 56 is shown and discussed, the laser tool 20 can include two or more extendable light paths 56, which may be spaced about the laser tool 20 in different circumferential or axial positions. In the illustrative laser tool 20 of FIGS. 7-9, the extendable light path 56 is one or more optic fibers 58 contained in a heat and impact resistant, protective shielding 60. Separate optic fibers 58 can be provided for transmission of the laser beam 26 and the emitted light 36, or the two can be multiplexed on the same optic fiber 58. The laser device 24 may shine the laser beam 26 directly into the optic fibers 58 or, as in FIG. 7, direct the laser beam 26 into the optic fibers 58 using a reflector 30 in a similar manner to that discussed above. The emitted light 36 may be directed into the emitted light receiver 38 directly from one of the optic fibers 58 and using a filter in the lens assembly 48 or, as in FIG. 8, may be directed through a dichroic reflector 30 in a manner similar to that discussed above.

Provision of an extendable light path 56 facilitates removing material deeper into the formation 12, because the extendable light path 56 transmits the laser beam 26 to the end wall of the material more efficiently than if the laser beam 26 were to travel through fluids in the well bore, particulate and other obstructions that may exist. As a result, the laser beam 26 attenuates less when transmitted through the extendable light path 56. Likewise, provision of an extendable light path 56 facilitates collecting emitted light 36 in instances, such as within deep perforations 22, where well fluids and other obstructions would attenuate the emitted light 36.

FIG. 7 depicts the extendable light path 56 extended into the formation 12 creating a perforation 22. FIG. 8 depicts emitted light being received through the extendable light path 56. FIG. 9 depicts the extendable light path 56 retracted into the laser tool 20. In this retracted configuration, the laser tool 20 may be inserted or withdrawn from the well bore 10 without the extendable light path 56 hanging up in the well bore 10.

One or more sensors 62, such as a pressure and a temperature sensor, can be provided on or near an end of the extendable light path 56 enabling the sensor 62 to be positioned in and collect data from within the hole when the extendable light path 56 is extended. The sensor 62 can communicate measurement data via the light path 56, for example multiplexed with the emitted light 36, or electrically within the shielding 60. The sensor 62 can be configured to communicate with the emitted light receiver 38 including the processor 44 and store measurement data on the computer readable media 46, or can be configured to transmit a signal representative of the measurement data via a link 40 to the surface. The processor 44 or a processor remote from the laser tool 20 can be configured to receive temperature measurements over time from the sensor 62 during the heating caused by the laser beam 26 and during the thermal decay period after the laser beam 26 has been inactivated. These time dependent thermal measurements can be used thereafter to determine formation thermal properties such as specific heat, thermal conductivity, and thermal diffusivity. Instructions for the processor 44 for use in determining the thermal properties can be stored on the computer readable media 46 as well as values representative of the determined properties for comparative and formation identification purposes. As is discussed in more detail below, information about the thermal properties of the formation can be used to alter laser drilling and/or perforating processes, including the selection of parameters associated with pulsing the laser.

The laser tool 20, as depicted in FIGS. 10 and 11, can be configured to utilize a fluid-based light path 68 through which the laser beam 26 and/or emitted light 36 can travel. The laser or acoustic signal from the distance meter 66 can be transmitted along the light path 68 (or light path 56 above). The fluid-based light path 68 can be, for example, a stream of optically transmissive fluid directed into the well bore 10 to displace less optically transmissive materials 72, such as drilling mud, well fluids, and entrained particulate, from the trajectory of the laser beam 26 or emitted light 36. In removal of material with the laser tool 20 or otherwise, the fluid-based light path 68 can operate to additionally remove cuttings. The fluid-based light path 68 can also impinge against the wall of the well bore 10 to clean the wall. Thus, for example, in an open hole well bore 10, the fluid-based light path 68 could remove a portion of the filter cake 74, i.e. drilling mud solids caked on the well bore wall 10, to reveal the formation 12. In the illustrative laser tool 20 of FIGS. 10 and 11, the fluid-based light path 68 is directed substantially coaxially with the laser beam 26 and substantially perpendicular to the longitudinal axis of the well bore. The fluid-based light path 68 can be directed to impact the wall of the well bore 10 substantially perpendicular to better clean the wall. However, it is also within the scope of the invention to direct the fluid-based light path 68 substantially parallel to the longitudinal axis of the well bore 10 and/or transverse to the path of the laser beam 26, or in another direction relative to the laser beam 26 and well bore 10. The fluid-based light path 68 can also operate to remove debris resulting from the material removal. Also, in FIGS. 10 and 11, the fluid-based light path 68 is depicted as expelled from the laser tool 20, but could also or alternatively be expelled from another source in the well bore 10.

The efficiency of the fluid-based light path 68 is a function of the optical transmission efficiency of the fluid. To increase the efficiency of the fluid-based light path 68, a fluid having a high optical transmission efficiency at the wavelength of the laser beam 26 or emitted light 36 can be selected. Water, certain oils, and mixtures or solutions including water and/or oil, are among many efficient optically transmissive fluids that can be used for the fluid-based light path 68. While water and oil are both liquids, the fluid need not be liquid. For example, the fluid-based light path 68 could be a gas, such as nitrogen at high pressure. The absorptivity of the fluid for the laser and LIBS Spectrum wavelengths should be taken into account during the selection of the fluid used in the light path. The fluid of the fluid-based light path 68 can be a dye which operates to amplify the laser power as the beam transmits through the dye in a manner similar to a dye laser system (ex. excimer dye laser).

The density of the fluid, as well as the speed at which it is expelled from the laser tool 20, may be selected to reduce the influence of outside factors on the path of the fluid-based light path 68. For example, as the drilling mud 72 circulates through the well bore 10 it can entrain the fluid-based light path 68, and, in the case of a light path 68 that is directed substantially perpendicular to the wall of the well bore 10, shift the light path 68 to impact the wall at an angle and at a different location that originally aimed. Likewise, impacts with larger particulate in the drilling mud 72 may attenuate or deflect the light path 68 from its trajectory. Such deflection and shift can be reduced by jetting the fluid at a high speed or even ultrasonic speed and/or by choosing a fluid that is dense. The density of the fluid, be it water, oil, or other, can be increased, if so desired, with a weighting agent, such as cesium salt, which results in a mixture which has acceptable transparency. Additionally, the circulation of fluids through the well bore 10 can be ceased during operation of the laser tool 20, or the laser tool 20 can be operated when circulation of fluids would otherwise be ceased, for example, while adding joints of pipe in the normal drilling process.

The influence of outside factors on the path of the fluid-based light path 68 can also be reduced by reducing the distance the light path 68 must span between the laser tool 20 and the material being removed or analyzed. The distance can be reduced by providing the outlet through which the fluid-based light path 68 is expelled close to the material being removed or heated, for example, by selection of the laser tool 20 diameter to be close to the diameter of the well bore 10 and/or provision of the outlet in a stabilizer fin 64 (FIG. 11). To the degree the fluid based light path 68 does shift or deflect, if the light path 68 remains continuous or any break in the light path 68 is insignificant, the laser beam 26 or emitted light 36 will still follow the path 68 and be transmitted between the material being removed or analyzed and the laser tool 20.

A reservoir 70 can be provided within the laser tool 20 or remote from the laser tool 20, for example in another component of the drill string or at the surface, to store fluid for the light path 68. A valve 76 can gate flow of fluid out of the laser tool 20. The valve 76 may be configured to operate as or incorporate a nozzle to consolidate the flow of fluid into a stream. A second valve 79 can be provided between the reservoir 70 and the valve 76 to control flow from the reservoir 70.

The fluid in the reservoir 70 can be pressurized or a secondary fluid in the reservoir 70 can be pressurized to expel the fluid of the fluid-based light path 68. Alternately or in combination with a pressurized reservoir 70, a pump 77 (FIG. 11) can be provided to pressurize the reservoir 70 to expel fluid or to pump fluid from the reservoir 70. The fluid in the reservoir 70 can be conserved by selecting the density of the fluid, the fluid-based light path 58 velocity, and the distance traversed by the light path 58 so that short pulses of fluid provide a transmission pathway of a duration long enough to communicate the laser beam 26 to the material being removed and/or the emitted light 36 to the laser tool 20. The fluid may be expelled in multiple pulses, for example, separate pulses to transmit the laser beam 26 to the formation and to receive the emitted light 36. In an embodiment where the laser beam 26 is pulsed, for example in a duty cycle, the fluid may be likewise pulsed. More or fewer pulses of different duration can be utilized as desired, as well as a single continuous flow, for example, transmitting the laser beam 26 to the formation, removing material, heating the formation to emit light, and transmitting the emitted light to the laser tool 20 during the single continuous flow.

Figure 13:
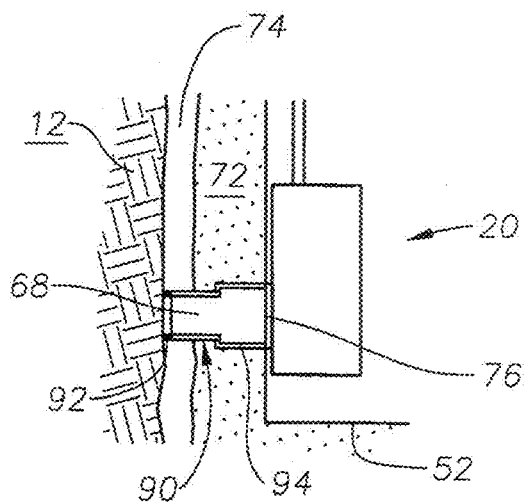
FIG. 13 is a detail side cross-sectional view of another illustrative laser tool constructed in accordance with the invention including provisions for an extendable snorkel shown extending from a housing of the laser tool.
Figure 14:
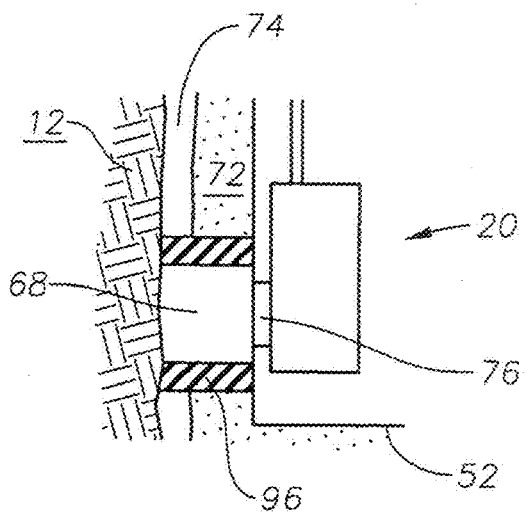
FIG. 14 is a detail side cross-sectional view of another illustrative laser tool constructed in accordance with the invention including provisions for an extendable snorkel utilizing an elastomeric body.

Referring to FIGS. 13 and 14, the laser tool 20 can be provided with a snorkel 90 extendable from a retracted position at least partially within the laser tool housing 52 or about the exterior surface of the laser tool housing 52 to an extended position, extending outward from the laser tool housing 52 into the well bore 10 and optionally into contact with the well bore 10 wall. Extending the snorkel 90 into contact with the well bore 10 wall can displace the filter cake 74 thereon, and enable more efficient transmission of the laser beam 26 into the formation 12. Also, in a configuration where the snorkel 90 will extend into contact with the well bore 10 wall, it may be desirable to provide a seal pad 92 at the end of the snorkel 90 to at least partially seal with the wall. FIG. 13 depicts an exemplary snorkel 90 including a plurality of rigid, concentrically nested, tubular bodies 94 that telescope to extend outward from a housing of the laser tool 20. FIG. 14 depicts an exemplary snorkel 90 including an elastomeric body 96 that is inflated or extruded to extend outward from the laser tool 20. Other configurations of snorkels 90 are within the scope of the invention. The snorkel 90 provides a passageway shielded from the flow of fluids and particulate in the well bore 10 through which the fluid-based light path 68, and thus laser beam 26 or emitted light 36, can pass substantially undisturbed. Dirty or optically lossy fluids trapped within the snorkel 90 may be displaced with optically transmissive fluids of the fluid-based light path 68. Using the space within the snorkel 68 aids in placement of the fluid-based light path 68 over using a flowing stream type fluid-based light path 68. It is also within the scope of the invention to utilize the snorkel 90 without the fluid-based light path 68 to shield passage of the laser beam 26 or emitted light 36. In one implementation omitting the fluid-based light path 68, the snorkel 90 can be substantially sealed against the wall of the well bore 10 and evacuated, for example, with a pump, to define a substantially unobstructed light path for the laser beam 26 or emitted light 36.

Figure 15:
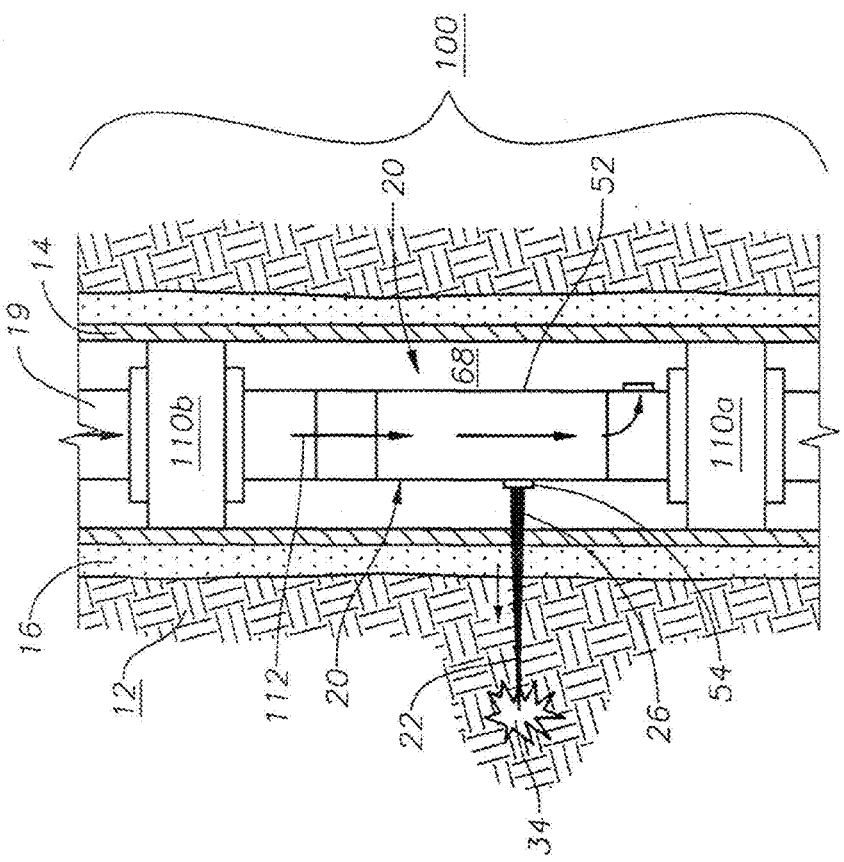
FIG. 15 is a view of an illustrative laser tool constructed in accordance with the invention including provisions for a fluid-based light path formed by at least partially flushing fluids and particulate from around the laser tool with optically transmissive fluid.

FIG. 15 depicts a laser tool 20 in use with a fluid-based light path 68 that is formed within an isolated zone 100 of the well bore 10. The zone is isolated by first actuating a seal 110, such as a packer, to seal the annulus between the string 19 and the interior wall of the well bore 10. In the illustrative implementation, the lower most seal 110*a* is actuated first; however, the upper most seal 110*b* could alternately be actuated first. The fluid 112 for the fluid-based light path 68 is introduced into the annulus to at least partially displace less optically transmissive fluids and particulate residing within the well bore 10. All of the less optically transmissive fluids and particulate need not be displaced, rather the fluid of fluid-based light path 68 can be introduced merely to increase the optical transmission efficiency between the laser tool 20 and the well bore 10. The fluid of the fluid-based light path 68 may be introduced from the surface, for example, through the interior of the string 19, into the annulus, or the fluid may be introduced from a reservoir in the string 19 as above. Once the desired improvement in optical transmission between the laser tool 20 and the well bore 10 is achieved, the upper seal 110*b* is actuated to isolate the zone 100. In some implementations, only an upper seal 110*a* is used, and a portion of the annular region below the upper seal 110*a* may be displaced with a fluid of desired optical properties. In some instances, this annular region may extend from the upper seal 110*a* to the bottom of the well bore 10. In some instances, a displacement fluid less dense than the ambient fluid being displaced may be used, the displacement fluid thereby floating above the ambient fluid and an amount of displacement fluid required being only that to result in a more transmissive optical path at the location of the laser beam 26.

Figure 16:
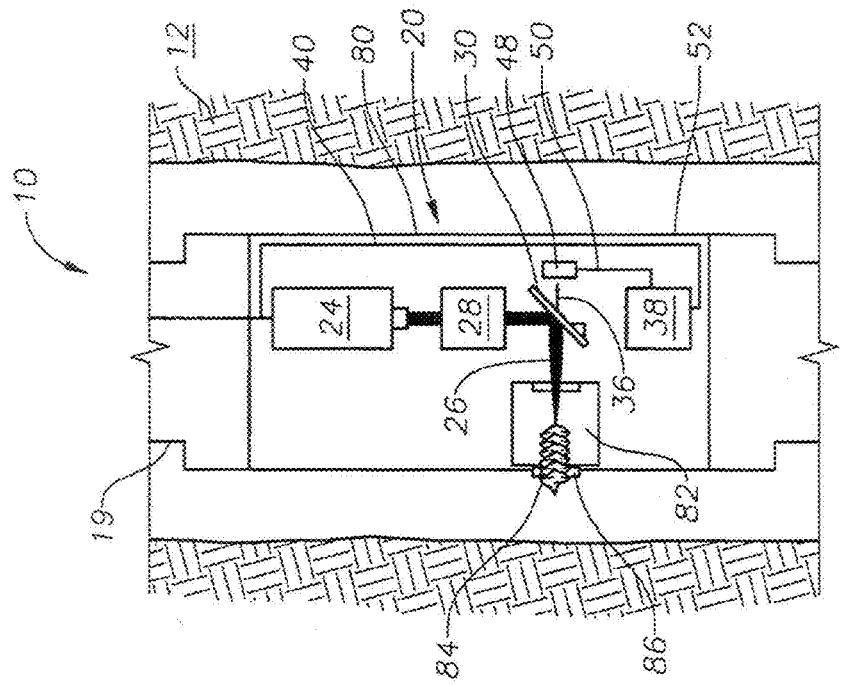
FIG. 16 is a side cross-sectional view of another illustrative laser tool having an internal chamber for analyzing material.

FIG. 16 depicts an alternate laser tool 80 configured for analysis of material within an analysis chamber 82 of the tool, and without directing the laser beam 26 into the well bore 10. The alternate laser tool 80 of FIG. 16 enables analysis of the formation 12 without removing a sample of the formation 12 from the well bore 10. The laser tool 80 includes a sample acquisition device 84, such as an Archimedes screw or rotary sidewall coring device as is well known in the art, that is extendable outward from the laser tool 80 and adapted to collect a sample of the material to be analyzed. It is within the scope of the invention to use other types of sample acquisition devices 84. In the case of an Archimedes screw, the screw bores into formation 12, removes a sample of the formation 12, and delivers the sample into the chamber 82. FIG. 16 depicts the sample acquisition device 84 partially extended. The sample acquisition device 84 may retract within the tool 80, or may otherwise fold or retract, to reduce the profile of the laser tool 80 for ingress and egress through the well bore 10. A seal 86 may be provided about the sample acquisition device 84 to prevent passage of fluids and particulate from the well bore 10, other than the sample being collected, into the chamber 82.

The laser beam 26 is focused within the analysis chamber 82 to heat the sample retrieved by the sample acquisition device 84. The sample is heated to emit light, and the emitted light is received by an emitted light receiver 38 for analysis (ex. spectrographic analysis) within the emitted light receiver 38 or remote from the tool 80. The seal 86 about the sample acquisition device 84 may substantially seal the chamber 82 so that the chamber 82 can be de-pressurized. Such lower pressure lowers the amount of energy required to heat the sample to emit light. As above, the laser beam device 24 can fire directly at the sample or, as depicted in FIG. 16, can fire into a reflector 30 that directs the laser beam 26 to the sample. If the laser beam device 24 fires into a reflector 20, the reflector 20 may be dichroic to reflect the laser beam 26 and pass emitted light 36 to the lens assembly 48 and to the emitted light receiver 38.

The laser tool 80 may be inserted into the well bore 10 on a wireline or inline in a tubing string 19 which may be continuous tubing or jointed pipe and may be a drilling string. The tubing string 19 may include other components, such as a drill bit or perforating tool.

Referring now to FIGS. 17-20, several methods according to the concepts described herein will be discussed.

Figure 17:
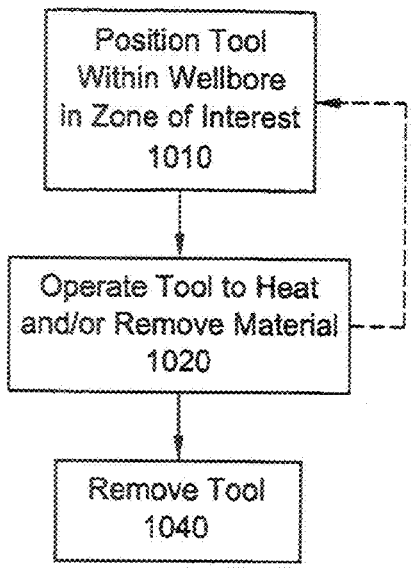
FIG. 17 is a flow diagram of an illustrative method of removing material in accordance with the invention.

With reference to FIGS. 1, 2 and 17 the laser tool 20 can be operated in heating or removing material. To wit, at block 1010 the laser tool 20 can be positioned in the well bore 10 in a zone of interest. In perforating, the laser tool 20 can be positioned within the well bore 10 at a depth corresponding to the general location of the desired perforations. In drilling, the laser tool 20 can be positioned where the drilling is to occur, for example at the surface to begin a new well bore 10 or within an existing well bore 10 to extend the existing well bore. If the laser tool 20 is provided with an extendable light path 58 (FIGS. 7-9) or used with a fluid based light path 68 (FIGS. 10-15), the light path 58, 68 can be deployed with the laser tool 20 in position as is discussed above.

At block 1020 the laser tool 20 is operated to direct a laser beam 26 to heat and/or remove material at one or more locations. Because the laser tool 20 can direct the laser beam 26 in multiple trajectories, material can be heated/removed in multiple locations about the well bore 10 without moving the tool 20. Likewise, by using multiple trajectories, material can be heated/removed in specified patterns, as well as to form shaped grooves and non-cylindrical perforations and as is discussed above. Material heating/removal at the one or more locations can be performed sequentially, i.e. by heating/removing material at one location until complete then heating/removing material at the next location, or material heating/removal at the one or more locations can be multiplexed as described above. The laser beam 26 can be focused to efficiently heat/remove material. If the laser tool 20 includes a fixed focusing array, the focal length can be set in relation to the distance between the laser tool 20 and the material being heated/removed. If the laser tool 20 incorporates an adjustable focusing array, the focal length can be set in relation to the distance between the laser tool 20 and the material being heated/removed, or can be dynamically adjusted as material is being removed. If dynamically adjusted, the focal length may be increased as the perforation or drilling goes deeper into the formation. For example, when perforating a cased well bore 10, the laser beam 26 can be first focused on the inner surface of the casing 14, and then the focal length increased to maintain focus on the material being removed as the perforation grows through the casing 14, cement 16, and into the formation 12. The distance meter 66 can be used in precisely determining the distance between the laser tool 20 and the material being removed, and the focal length can be set in relation to the measured distance.

After performing block 1020, i.e. operating the laser tool 20 to heat and/or remove material at the one or more locations, operations may return to block 1010 and the laser tool 20 be repositioned within the well bore 10 at a different depth within the zone of interest or within another zone of interest. Thereafter blocks 1020 and 1010 may be repeated as desired. When operations are complete, or if it is otherwise desired to permanently or temporarily cease material heating/removal, the laser tool 20 is removed from the well bore 10 at block 1040.

Figure 18:
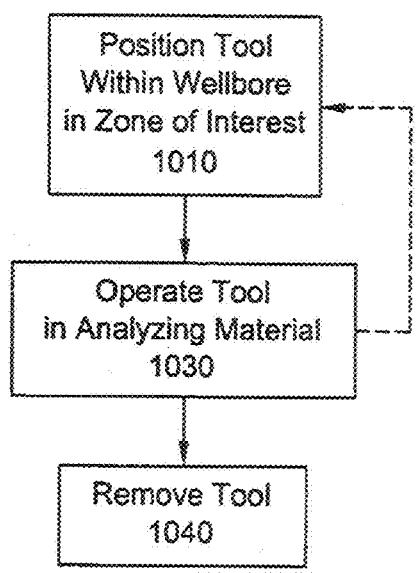
FIG. 18 is a flow diagram of an illustrative method of analyzing material in accordance with the invention.
Figure 19:
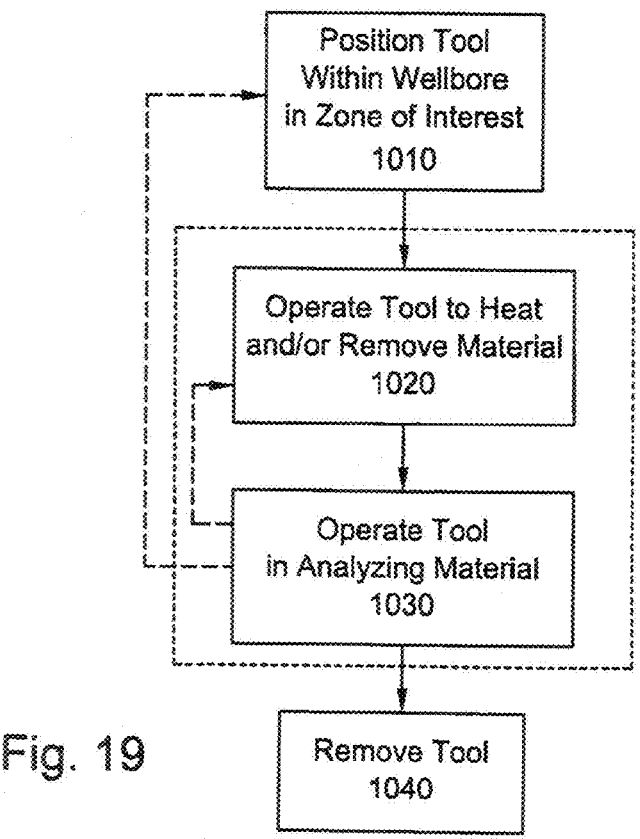
FIG. 19 is a flow diagram of an illustrative method of heating and/or removing material and analyzing material in accordance with the invention.

With reference to FIGS. 3 and 18, the laser tool 20 or another tool having an emitted light receiver 38 (with or without the laser generator 24, focusing array 28, or reflector 30) can be operated in analyzing material within the well bore. In such operation, at block 1010 the tool can be positioned in the well bore 10 in a zone of interest. The tool can be positioned to receive emitted light 36 from a heated portion of the material being analyzed, for example the formation 12. If the laser tool 20 is provided with an extendable light path 58 (FIGS. 7-9) or used with a fluid based light path 68 (FIGS. 10-15), the light path 58, 68 can be deployed when the laser tool 20 is in position as is discussed above.

At block 1030 the tool is operated to receive emitted light 36 from the material within the well bore. The emitted light 36 may be received from one or more locations within the well bore. The received emitted light 36 may be used in analyzing the material. The analysis may take place within the tool, for example by providing the emitted light receiver 38 adapted to determine one or more chemical, physical, or state characteristics of the material from the emitted light. Alternately the analysis may take place elsewhere, for example, as discussed above by transmitting the emitted light 36 or a signal indicative of the emitted light 36 to an analysis device on the surface.

After performing block 1030, i.e. operating the tool in analyzing material, operations may return to block 1010 and the tool repositioned within the well bore 10 at a different depth within the zone of interest or within another zone of interest. Thereafter, blocks 1030 and 1010 may be repeated as desired. The tool is removed from the well bore 10 at block 1040, for example when the material analysis is complete, or if it is otherwise desired to permanently or temporarily cease receiving emitted light 36.

With reference to FIGS. 1-3 and 19, the laser tool 20 can be operated in both analyzing material as well as removing and/or heating material. Accordingly, the laser tool 20 can be positioned in the well bore 10 in a zone of interest as described above with respect to block 1010. Thereafter, the laser tool 20 can be operated to direct a laser beam 26 to heat and/or remove material at one or more locations as described above with respect to block 1020. At block 1030, the laser tool 20 can be operated to receive emitted light 36 from the material being heated and received emitted light to be used in analyzing the material. Blocks 1020 and 1030 may be performed sequentially or concurrently.

Figure 20:
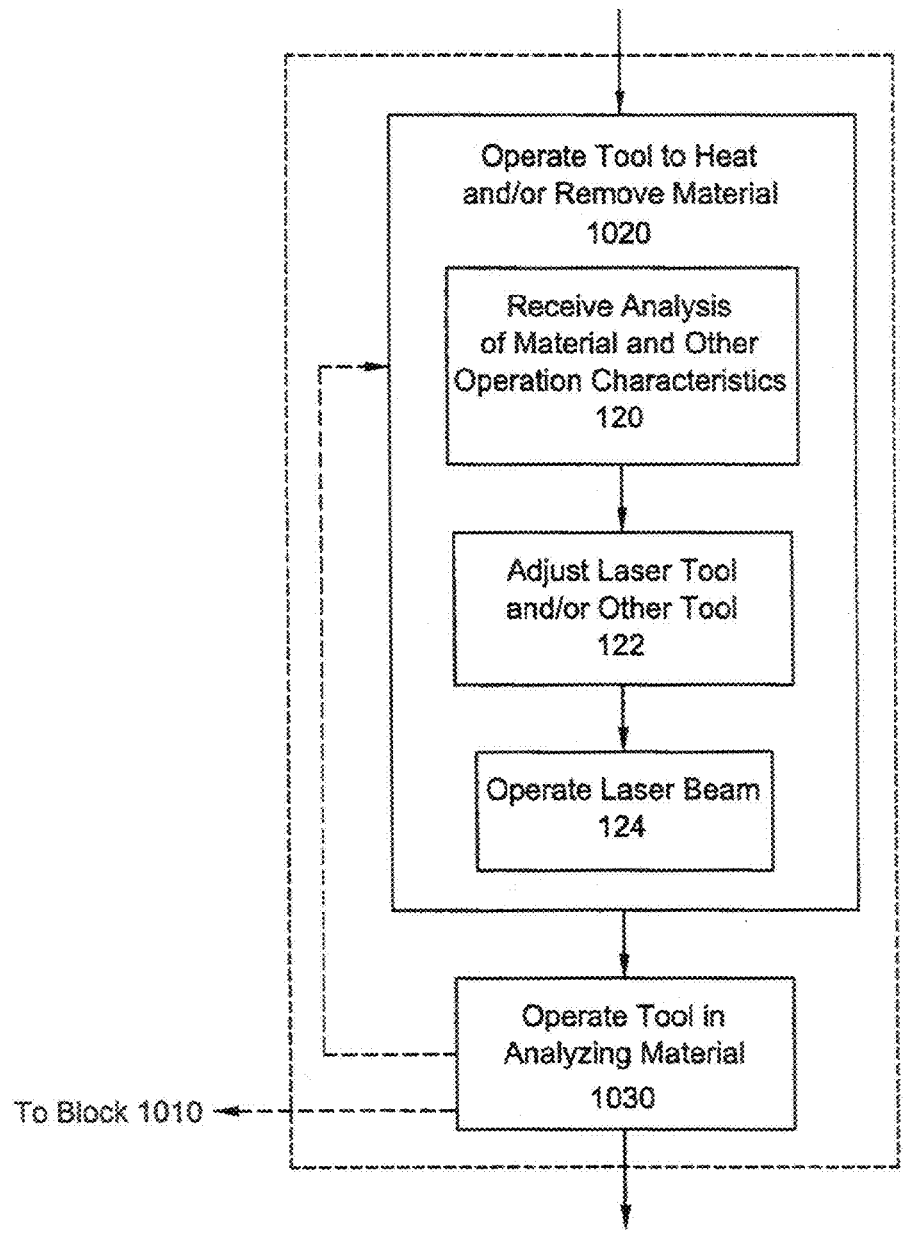
FIG. 20 is a flow diagram showing optional substeps of the flow diagrams of FIG. 18 or 19.

As better seen in FIG. 20, the analysis, alone or together with additional information, can be used in a feedback loop for adjusting the operation of the laser tool 20. In one instance the analysis can provide a qualitative or quantitative indication of the efficiency of the material removal process itself, including providing information indicative of the mode of material removal, the depth of material removal, the rate of material removal, and other information. For example, the analysis may encompass measuring the total intensity of emitted light over a broad-spectrum (for example, visible light and above), to infer whether a greater or lesser volume of material has been heated by the laser beam 26. A greater volume of the material having been heated by the laser beam 26 may be indicative of heating in a melting or vaporizing mode of material removal. A lesser volume of material being heated may correlate with a spalling mode of material removal. As discussed above, in a spalling mode of material removal a relatively concentrated volume of material is heated causing the material (e.g. formation rock) to fracture with resultant removal of a relatively larger portion of the material. In a like manner, information obtained from the analysis can be used in improving the quality of the data collected and aid in interpretation of information obtained about the formation.

The feedback loop can also operate in determining the most effective or desired locations for material removal, such as to determine the location of further drilling or perforating, or for example the location for future wells. The analysis can encompass determining indications of lithology, formation hardness, competency, porosity, permeability, specific heat, thermal conductivity, thermal diffusivity and other factors which may be useful to be considered in locating the well bore or perforation path or improving drilling efficiency to a target, formation exposure within the target, and/or other production related goals. Such information may be useful in determining that boundaries above or below a target formation have been or are being encountered or to recognize a "sweet spot" within a target sand. Physical formation properties which may be useful for targeting or steering purposes such as porosity, permeability, hardness or competency may be inferred from the chemical characteristic during the material removal process, as well as from the material removing efficiency as discussed above.

In either instance above, the additional information can include information detected from additional sensors in the well bore 10, such as the sensors 62 optionally included on light path 58 or the distance meter 66. In one implementation, the additional information can include information related to the topography of the well bore and/or the depth and location of perforations and drilled bores. Such topography can be determined using the distance meter 66. For example, the distance meter 66 may be operated to determine the depth of one or more perforations or bores and/or the distance to one or more points on the wall of the well bore, for example by raster scanning, to determine a distance profile of an area of the well bore in relation to one or more axis. From such scanning, a spatial concentration or grading of the material removed can be inferred, and may be used to map the resultant perforated or drill holes. Further this multipoint distance scanning may be used to identify geometric shapes and/or textures indicative of cobbles or refractory materials, which too may be an indication of drilling or perforating progress or an indication of the type of material being removed. The additional information can include information detected from additional sensors in the well bore 10, such as the sensors 62 optionally included on light path 58.

Accordingly, with reference to FIG. 20, at block 120 the analysis of the material and other operation characteristics are received. At block 122, an adjustment to the laser tool 20 can determined and thereafter the laser tool 20 adjusted. Such adjustments may include numerous adjustments that can be made to the operation of the laser tool 20, for example, adjusting the energy, power, frequency, duty cycle, trajectory and focal point of the laser beam 26. Alternately, or in combination with adjusting the laser tool 20, an adjustment to another tool can be determined and applied. For example, in a drilling operation with a drilling bit or a perforating operation with a perforating tool, adjustments can be made to the operations in relation to the analysis of the material and other operational characteristics.

At block 124, the laser beam is operated to remove/heat material using the updated laser tool 20 configuration. The method can cycle between blocks 1020 and 1030 as many times as desired. The feedback loop depicted in FIG. 20 can be implemented entirely by machine processes (i.e. a computer downhole or at the surface), by combination of machine processes and human interaction, or simply by a human operator receiving the data and thereafter adjusting the operation of the laser tool. The determination of the laser tool 20 adjustment can occur as changes in the analysis or additional information that would require adjustment are detected. Alternately, the determination of the laser tool 20 adjustment can occur continuously, in regular intervals, or in irregular intervals during the operations.

Referring again to FIG. 19, after performing block 1030; i.e. operating the tool in analyzing material, operations may return to block 1010 and the tool repositioned within the well bore 10 at a different depth within the zone of interest or within another zone of interest. Thereafter, blocks 1010, 1020, and 1030 may be repeated as desired. The tool is removed from the well bore 10 at block 1040, for example when operations are complete, or if it is otherwise desired to permanently or temporarily cease operations.

Various configurations of the disclosed invention are available and are not meant to be limited only to the configurations disclosed in this specification. Even though numerous characteristics and advantages of the present invention have been set forth in the foregoing description together with details of illustrative implementations, the disclosure is illustrative only and changes may be made within the principle of the invention. It is therefore intended that such changes be part of the invention and within the scope of the following claims.

What is claimed is:

1. A system for use in transmitting light in a well bore, comprising:
    a seal adapted to substantially seal circumferentially around the well bore, and when substantially sealing, define an end of an isolated zone of the well bore;
    a fluid light path comprising a fluid supplied into the isolated zone, the fluid adapted to displace less optically transmissive fluid residing in the well bore; and
    at least one of a laser device adapted to output a laser beam at least partially overlapping the fluid light path or an emitted light receiver adapted to receive light emitted by a heated material at least partially through the fluid light path.

2. The system of claim 1, further comprising:
    a second seal adapted to substantially seal circumferentially around the well bore, and being axially offset from the first mentioned seal; and
    wherein the fluid light path comprises a fluid supplied into the isolated zone between the seals.

3. The system of claim 1, further comprising:
    a fiber optic array comprising a plurality of optical fibers arranged to receive the laser beam.

4. The system of claim 3, wherein each optical fiber is adapted to direct the laser beam in a different trajectory.

5. The system of claim 3, wherein the optical fibers are arranged to receive the laser beam in fewer than all of the plurality of optical fibers at a time.

6. The system of claim 3, wherein the fiber optic array directs the laser beam in a rectangular, oval or circular pattern.

7. The system of claim 1, further comprising a fluid reservoir within the well bore containing the fluid of the fluid light path.

8. The system of claim 1, further comprising a conduit in communication with a fluid reservoir containing the fluid of the fluid light path and residing outside of the well bore.

9. The system of claim 1, wherein the fluid comprises a gas.

10. The system of claim 1, wherein the fluid displaces less than all of the fluids residing in the isolated zone.

11. The system of claim 1, further comprising:
    a laser device adapted to output a laser beam;
    one or more sensors in the wellbore; and
    a computer automatically operable to adjust the laser beam in response to the sensors.

12. A method of communicating light between a device positioned in a well bore and the earth formation, the method comprising:
    actuating a seal in the well bore to define an end of an isolated zone of the wellbore;
    receiving an optically transmissive fluid in the isolated zone and displacing less optically transmissive fluid residing in the well bore; and
    transmitting light between the earth formation and the device through the optically transmissive fluid.

13. The method of claim 12, further comprising:
    actuating a second seal axially offset from the first mentioned seal to define a second end of the isolated zone of the well bore.

14. The method of claim 12, wherein transmitting light comprises directing the light through a fiber optic array comprising a plurality of optical fibers.

15. The method of claim 14, comprising directing the light in a plurality of different trajectories using the plurality of optical fibers.

16. The method of claim 14, comprising directing the light through fewer than all of the plurality of optical fibers.

17. The method of claim 14, comprising transmitting the light in a rectangular, oval or circular pattern.

18. The method of claim 12, wherein receiving an optically transmissive fluid in the isolated zone comprises receiving the optically transmissive fluid from a reservoir in the well bore.

19. The method of claim 12, wherein receiving an optically transmissive fluid in the isolated zone comprises receiving the optically transmissive fluid from a reservoir outside of the well bore.

20. The method of claim 12, further comprising:
    sensing information in the well bore; and
    automatically adjusting the light in response to the information sensed.

21. The method of claim 12, wherein the optically transmissive fluid comprises a gas.

22. The method of claim 12, further comprising outputting a laser beam from a laser device in the well bore to remove at least a portion of formation rock, a well bore casing, or a wellbore cement.

23. The method of claim 22, further comprising directing the laser beam towards at least one of a side wall of the well bore or a bottom of the well bore to remove subterranean material during a drilling operation.

24. A system for use in transmitting light in a well bore, comprising:
    a seal adapted to substantially seal circumferentially around the well bore, and when substantially sealing, define an end of an isolated zone of the well bore;
    a fluid light path comprising a fluid supplied into the isolated zone, the fluid adapted to displace less optically transmissive fluid residing in the well bore; and
    a second seal adapted to substantially seal circumferentially around the well bore, and being axially offset from the first mentioned seal,
    wherein the fluid light path comprises a fluid supplied into the isolated zone between the seals.

25. A system for use in transmitting light in a well bore, comprising:
    a seal adapted to substantially seal circumferentially around the well bore, and when substantially sealing, define an end of an isolated zone of the well bore;

a fluid light path comprising a fluid supplied into the isolated zone, the fluid adapted to displace less optically transmissive fluid residing in the well bore;

a laser device adapted to output a laser beam; and a fiber optic array comprising a plurality of optical fibers arranged to receive the laser beam.

26. A method of communicating light between a device positioned in a well bore and the earth formation, the method comprising:

actuating a seal in the well bore to define an end of an isolated zone of the wellbore;

receiving an optically transmissive fluid in the isolated zone and displacing less optically transmissive fluid residing in the well bore;

transmitting light between the earth formation and the device with the optically transmissive fluid; and actuating a second seal axially offset from the first mentioned seal to define a second end of the isolated zone of the well bore.

27. A method of communicating light between a device positioned in a well bore and the earth formation, the method comprising:

actuating a seal in the well bore to define an end of an isolated zone of the wellbore;

receiving an optically transmissive fluid in the isolated zone and displacing less optically transmissive fluid residing in the well bore; and transmitting light between the earth formation and the device with the optically transmissive fluid, wherein transmitting light comprises directing the light through a fiber optic array comprising a plurality of optical fibers.

* * * * *